(12) United States Patent
Stein et al.

(10) Patent No.: US 7,074,769 B2
(45) Date of Patent: Jul. 11, 2006

(54) OLIGONUCLEOTIDE INHIBITORS OF BCL-XL

(75) Inventors: Cy A. Stein, New City, NY (US); Paul Cossum, The Woodlands, TX (US); Robert Rando, Annandale, NJ (US); Joshua Ojwang, Edmond, OK (US)

(73) Assignees: The Trustees of Columbia University in the City of New York, New York, NY (US); Aronex Pharmaceuticals, Inc., Lexington, MA (US)

( * ) Notice: Subject to any disclaimer, the term of this patent is extended or adjusted under 35 U.S.C. 154(b) by 186 days.

(21) Appl. No.: 09/753,169

(22) Filed: Jan. 2, 2001

(65) Prior Publication Data

US 2003/0017196 A1    Jan. 23, 2003

Related U.S. Application Data

(63) Continuation of application No. PCT/US99/15250, filed on Jul. 2, 1999, which is a continuation-in-part of application No. 09/109,614, filed on Jul. 2, 1998, now abandoned.

(51) Int. Cl.
  *A01N 43/04*   (2006.01)
  *A61K 31/70*   (2006.01)
  *C07H 21/00*   (2006.01)
  *C07H 21/04*   (2006.01)

(52) U.S. Cl. ............... 514/44; 536/24.3; 536/24.31; 536/24.33; 536/24.5

(58) Field of Classification Search ............... 536/23.1, 536/24.3, 24.31, 24.33, 24.5; 435/6, 37, 435/458; 514/44
See application file for complete search history.

(56) References Cited

U.S. PATENT DOCUMENTS

| | | | |
|---|---|---|---|
| 5,023,243 A | | 6/1991 | Tullis |
| 5,107,065 A | | 4/1992 | Schewmaker et al. |
| 5,496,547 A | | 3/1996 | Lam et al. |
| 5,502,177 A | * | 3/1996 | Matteucci et al. ......... 536/26.6 |
| 5,583,034 A | | 12/1996 | Green |
| 5,587,470 A | | 12/1996 | Cook et al. |
| 5,593,974 A | | 1/1997 | Rosenberg et al. |
| 5,618,704 A | * | 4/1997 | Sanghvi et al. ............ 435/91.5 |
| 5,670,633 A | | 9/1997 | Cook et al. |
| 5,689,052 A | | 11/1997 | Brown et al. |
| 5,702,897 A | | 12/1997 | Reed et al. |
| 5,734,033 A | | 3/1998 | Reed et al. |
| 5,776,905 A | * | 7/1998 | Gibbons et al. ............... 514/44 |
| 5,792,615 A | * | 8/1998 | Arnold et al. .................. 435/6 |
| 5,843,713 A | | 12/1998 | Yoshida et al. |

FOREIGN PATENT DOCUMENTS

| | | | |
|---|---|---|---|
| WO | WO 9307883 A1 | * | 4/1993 |
| WO | WO 95/08350 A | | 3/1995 |
| WO | WO 9508350 A1 | * | 3/1995 |
| WO | 9515400 | | 6/1995 |
| WO | 9805777 | | 2/1998 |

OTHER PUBLICATIONS

Crooke Basic Principles of Antisense Therapeutics, Chapter 1, Antisense Research and Application, Jul. 7, 1998, Springer-Verlag, Berlin, Heidelber, New York, pp. 1-50.*

Branch, A good antisense molecule is hard to find. TIBS, Feb. 1998, pp. 45-50.*

Jen et al. Suppression of Gene Expression by argeted Disruption of Messenger RNA: Available Options and Current Strategies Stem Cells, 2000, vol. 18, pp. 307-319.*

MJ Pollaman et al., Nature Medicine, "Inhibition of neointimal cell bcl-x expression induces apoptosis and regression of vascular disease." Feb. 1998, vol. 4, No. 2, pp. 222-227.*

(Continued)

*Primary Examiner*—Janet L. Epps-Ford
(74) *Attorney, Agent, or Firm*—John P. White, Esq.; Cooper & Dunham LLP

(57) ABSTRACT

This invention provides an antisense oligonucleotide or analog thereof comprising 10 or more contiguous bases or base analogs from the sequence of bases of sequence A, B, C, D, E, F, G, H, I, J, K, L, or M of FIG. 1. This invention also provides the above-described antisense oligonucleotides, wherein the nucleotide sequence comprises nucleotide sequence A, A', B, C, C', D, E, E, E', F, G, G', H, H', I, I', J, K, K', L, L', M, or M' of FIGS. 2A and 2B. This invention also provides the above-described antisense oligonucleotides, wherein the oligonucleotide is encapsulated in a liposome or nanoparticle. This invention also provides the above-described antisense oligonucleotides, wherein the phosphate backbone comprises phosphorothioate bonds. In addition, this invention provides a method of treating cancer, comprising introducing into a tumor cell an effective amount of the the above-described antisense oligonucleotide, thereby reducing the levels of bcl-xL protein produced and treating cancer. This invention also provides the above-described methods, wherein the introducing comprises using porphyrin or lipofectin as a delivery agent. This invention also provides the above-described pharmaceutical compositions, wherein the oligonucleotide is encapsulated in a liposome or nanoparticle. This invention further provides the above-described pharmaceutical compositions, wherein the pharmaceutical composition comprises tetra meso-(4-methylpyridyl)porphine or tetra meso-(anilinium)porphine or a combination thereof.

3 Claims, 22 Drawing Sheets

OTHER PUBLICATIONS

X: Copies of these references were previously fowarded to Applicants during the prosecution of related application, 09/832,648.*

Goodchild, J. Bioconjugate Chemistry. vol. 1, No. 3, pp. 165-187. May/Jun. 1990.*

Agrawal, S., et al., Proc. Natl. Acad. Sci. U.S.A. (1988) vol. 85:7079-7083.

Antisense'97: A roundtable on the state of the industry. Nature Biotechnology 15 (Jun. 1997): 519-524.

Beaucage, S., and Caruthers, M., Tetrahedron Lett. (1981) vol. 22:1859-1862.

Cook, P.D., "Medicinal Chemistry of Antisense Oligonucleotides—future opportunities" (1991) Anti Cancer Drug Design vol. 6:585:-607.

Crooke, S.T. Vitravene—Another piece in the Mosaic. Antisense and Nucleic Acid Drug Dev. 8(1998):vii-viii.

Gewritz et al. Facilitating oligonucleotide delivery: Helping antisense deliver on it s promise. Proc. Natl. Acad. Sci. USA 93 (Apr. 1996); 3161-3163.

Ghosh, S., et al., J. Biol. Chem. (1990) vol. 265:2935-2940.

Gura, T. Antisense has growing pains. Science 270 (Oct. 1995): 575-577.

Hemken, P., et al., J. Biol. Chem. (1992) vol. 267:9948-0057.

Iverson, P., Anti-Cancer Drug Des. (1991) vol. 6:531-538.

Krajewska, M. et al. "Immunohistochemical analysis bcl-2, bax, bcl-x, and mcl-1 expression in prostate cancer." Am. J. Pathol. (1996) vol. 148:1567-1576.

Luedeke, G.H., Ziegler, Al., Stahel, R.A., and Zangemeister-Wittke, U., "Antisense oligonucleotides targeting sequences shared by the Bcl-2 and the Bcl-xL mRNA efficiently downregulate expression of both proteins and induce apoptosis of lung cancer cells." Division of Oncology, Department of Internal Medicine, University Hospital, CH-8091 Zurich, Switzerland. (Abstract #1140 from 88 Ann. Meet. AACR, Apr. 12-16, 1997, vol. 38, (Mar. 1997), p. 171).

Milligan et al., "Current Concepts in Antisense Drug Design" Journal of Medicinal Chemistry (Jul. 9, 1993) vol. 36:1924-1937; Pollman et al., "Inhibition of neointimal cell bcl-x expression induces apoptosis and regression of vascular disease." Nature Medicine (1998) vol. 4:222-227.

Ratajczak, et al., Proc. Natl. Acad. Sci. U.S.A. (1992) vol. 89:11823.

Rojanasakul, Y. Antisense oligonucleotide therapeutics: Drug delivery and targeting. Adv. Drug delivery rev. 18(1996: 115-131.

Stein, C.A. Keeping the biotechnology of antisense in context. Nature Biotechnology 17(Mar. 1999):209.

Stull et al. Antigene, ribozyme and aptamer nucleic acid drugs: Progress and prosepcts. Pharm. Res. 12 (Apr. 1995): 465-483.

Uhlmann, E. And Peyman A., "Antisense Oligonucleotides: A New Therapeutic Principle" Chem. Rev. (1990) vol. 90:544-579.

Wang, Z. et al., "Induction of bcl-xl by CD40 Engagement Rescues slg-induced Apoptosis in Murine B Cells", The Journal of Immunology (1995) vol. 155:3722-3725.

Zhao, Q., et al., Antisense Research and Development (1993) vol. 3:53-66.

Zon, G., "Oligonucleotide Analogues as Potential Chemotherapeutic Agents," Pharmaceutical Research (Nov. 9, 1988) vol. 5:539-549.

U.S. Appl. No. 09/832,633, Stein et al., filed Apr. 4, 2001.

U.S. Appl. No. 10/160,344, Stein et al., filed May 31, 2002.

Amarente-Mendes, G.P. et al. (1998), "Bcl-2 Independent BCR-ABL-mediated Resistance to Apoptosis: Protection is Correlated with Up-Regulation of Bcl-XL" Oncogene, 16:1383-13.

Leech G.H. et al. (1998), Antisense Oligodeoxynucleotides Designed to Downregulate the Expression of Bcl-XL and . . . Proc. Ann. Meet. Am. Assoc. Canc. Res. NY, 39:417.

Luedke G.H et al. (1997), Antisense Oligonucleotides Targeting Sequences Shared by the Bcl-2 and the Bcl-XL mRNA . . . Proc. Ann. Meet. Am. Assoc. Canc. Res. NY, 38:A1140.

Crooke S.T. (1998), "Basic principles of Antisense Therapeutics" Antisense research and Applications, CRC Press, pp. 1-50.

* cited by examiner

Figure 1

A. ctc aac cag tcc att gtc ca

B. tcc cgg ttg ctc tga gac at

C. gcc aca gtc atg ccc gtc ag

D. ctg cga tcc gac tca cca at

E. agt cct gtt ctc ttc cac

F. ctt tac tgc tgc cat ggg

G. cgc cgt tct cct gga tcc aa

H. ctg act cca gct gta tcc

I. ggt ctc cat ctc cga ttc

J. cct ggg gtg atg tgg agc

K. agt tcc aca aaa gta tcc

L. ctt tcg gct ctc ggc tgc

M. aac cag cgg ttg aag cgt

Figure 2A

A.   (T31028)
     c*t*c* aac* cag t*c*c at*t gt*c* c*a

A'.  (T31029)
     C*T*C* aaC* Cag T*C*C aT*T gT*C* C*a

B.   (T31030)
     t*c*c* cgg t*tg c*t*c* tga ga*c* a*t

C.   (T31044)
     g*c*c* aca gt*c atg c*c*c gt*c* a*g

C'.  (T31045)
     g*C*C* aCa gT*C aTg C*C*C gT*C* a*g

D.   (T31049)
     CT*g Cga T*C*C gaC* T*Ca C*C*a* a*t

E.   (T31054)
     a*g*t* c*c*t gt*t c*t*c t*t*c* c*a*c

E'.  (T31055)
     a*g*T* C*C*C* g*T*T C*T*C T*T*C* C*a*c

F.   (T31061)
     C*T*T* TaC TgC* TgC* CaT* g*g*g

G.   (T31043)
     C*gC* C*gT* T*C*T* C*C*T gga TC*C* a*a

G'.  (T31042)
     c*gc* c*gt* t*c*t* c*c*t gga tc*c* a*

Figure 2B

H.  (T31053)
    C*T*g* aC*T* C*Ca gC*T gTa* T*C*c

H'. (T31052)
    c*t*g* ac*t* c*ca gc*t gta* t*c*c

I.  (T31057)
    g*g*T* CT*C* CaT* CT*C Cga* T*T*c

I'. (T31056)
    g*g*t* ct*c* cat* ct*c cga* t*t*c

J.  (T31062/63)
    c*c*t* ggg gtg* atg* tgg* a*g*c

K.  (T31065)
    a*g*T* TC*C aC*a aaa gT*a* T*C*c

K'. (T31064)
    a*g*t* tc*c ac*a aaa gt*a* t*c*c

L.  (T31067)
    C*T*T* Tcg gC*T C*T*C ggC* T*g*c

L'  (T31066)
    c*t*t* tcg gc*t c*t*c ggc* t*g*c

M.  (T31069)
    a*a*C* Cag Cgg T*Tg aag* C*g*t

M'. (T31068)
    a*a*c* cag cgg t*t*g aag* c*g*t where  * = phosphorothioate
           C = Propynyl dC
           T = Propynyl dT Figure 3A
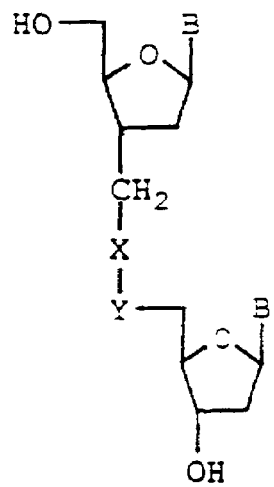
|  | X | Y |
|---|---|---|
| Hydroxylamine | N-H | O |
| MOMI | O | N-CH₃ |
| MMI | N-CH₃ | O |
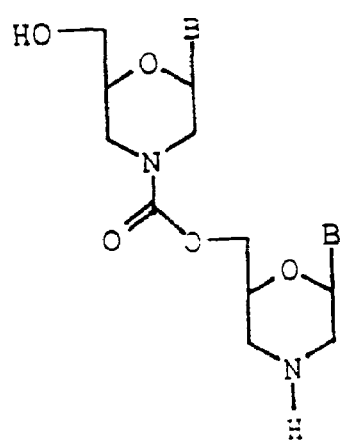
Morpholino-carbamate

Figure 3B
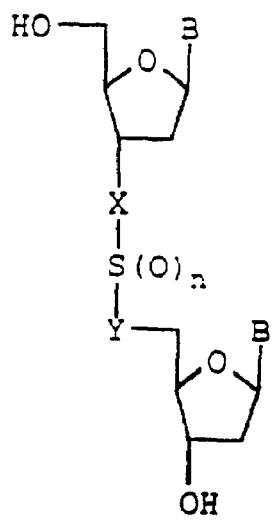
| n = 2 | X | Y |
|---|---|---|
| Sulfate | O | O |
| Sulfonate | O | CH₂ |
| Sulfone | CH₂ | CH₂ |
| Sulfamate | O | NH |
| Sulfonamide | NH | CH₂ |
| n = 1 | X | Y |
|---|---|---|
| Sulfite | O | O |
| Sulfoxide | CH₂ | CH₂ |
| n = 0 | X | Y |
|---|---|---|
| Sulfide | CH₂ | CH₂ |
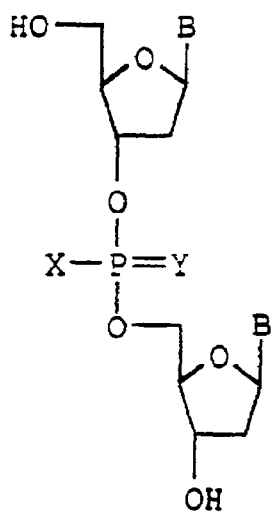
| | X | Y |
|---|---|---|
| Phosphodiester | O | O |
| Phosphorothioate | S | O |
| Phosphorodithioate | S⁻ | S |
| Methylphosphonate | CH₃ | O |
| Phosphotriester | O-R | O |
| Phosphoramidate | NH-R | O |
| Boranophosphate | BH₃ | O |

Figure 3C
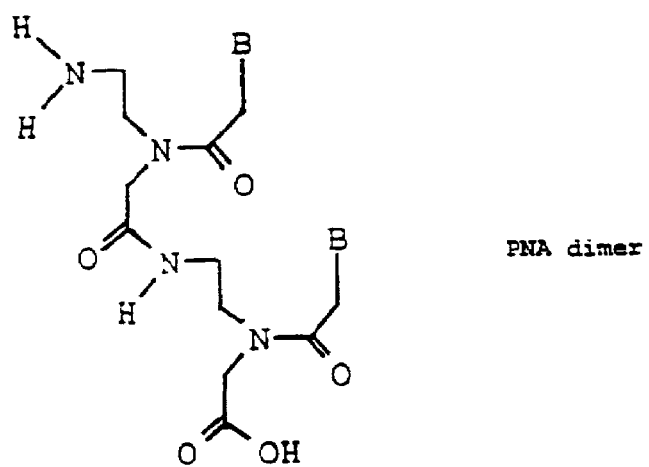
PNA dimer
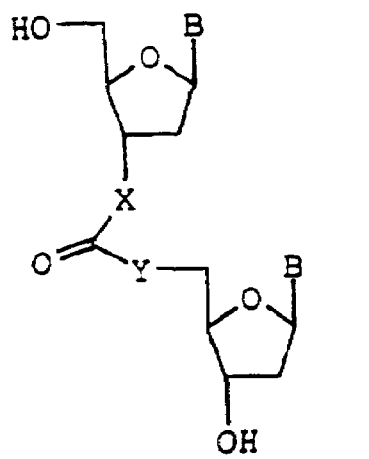
Carbonate
5'-N-carbamate

|  | X | Y |
|---|---|---|
| Formacetal | O | O |
| 5'-Thioether | CH₂ | S |
| 3'-Thioformacetal | S | O |
| 5'-Thioformacetal | O | S |

X = BIOTIN
= CHOLIC ACID
= FLUORESCEIN

2'-O-(AMINOPENTYL) ADENINE
CONJUGATES

Figure 5A
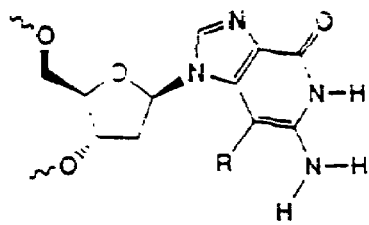
3-DEAZAGUANINES
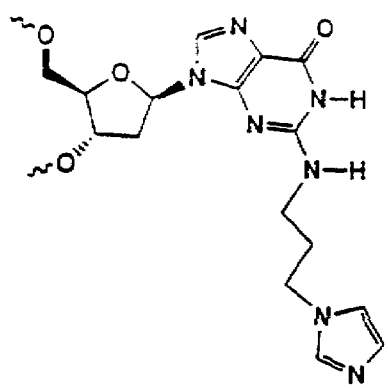
N2-IMIDAZOLYLPROPYL
GUANINE
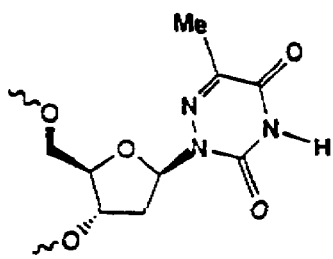
6-AZATHYMIDINE
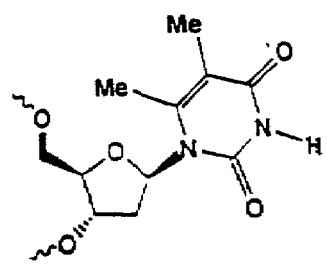
5,6-DIMETHYLTHYMIDINE
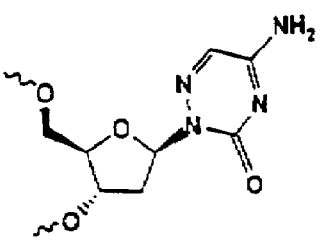
6-AZA-DEOXYCYTIDINE Figure 5B
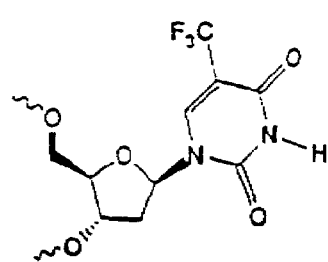
TRIFLUOROTHYMINE
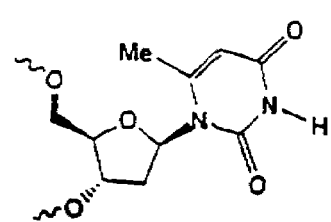
6-METHYLTHYMIDINE
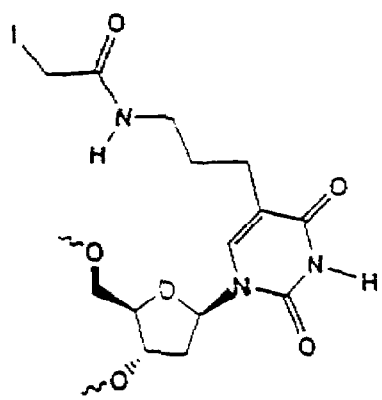
IODOACETAMIDOPROPYL URACIL
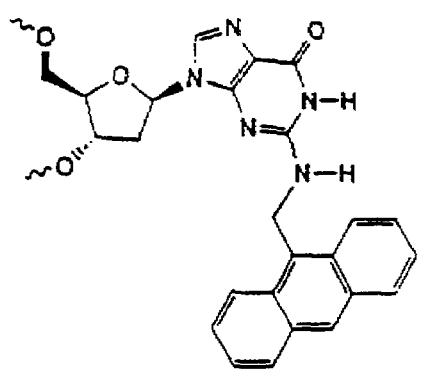
N2-ANTRACENYLMETHYL
GUANINE

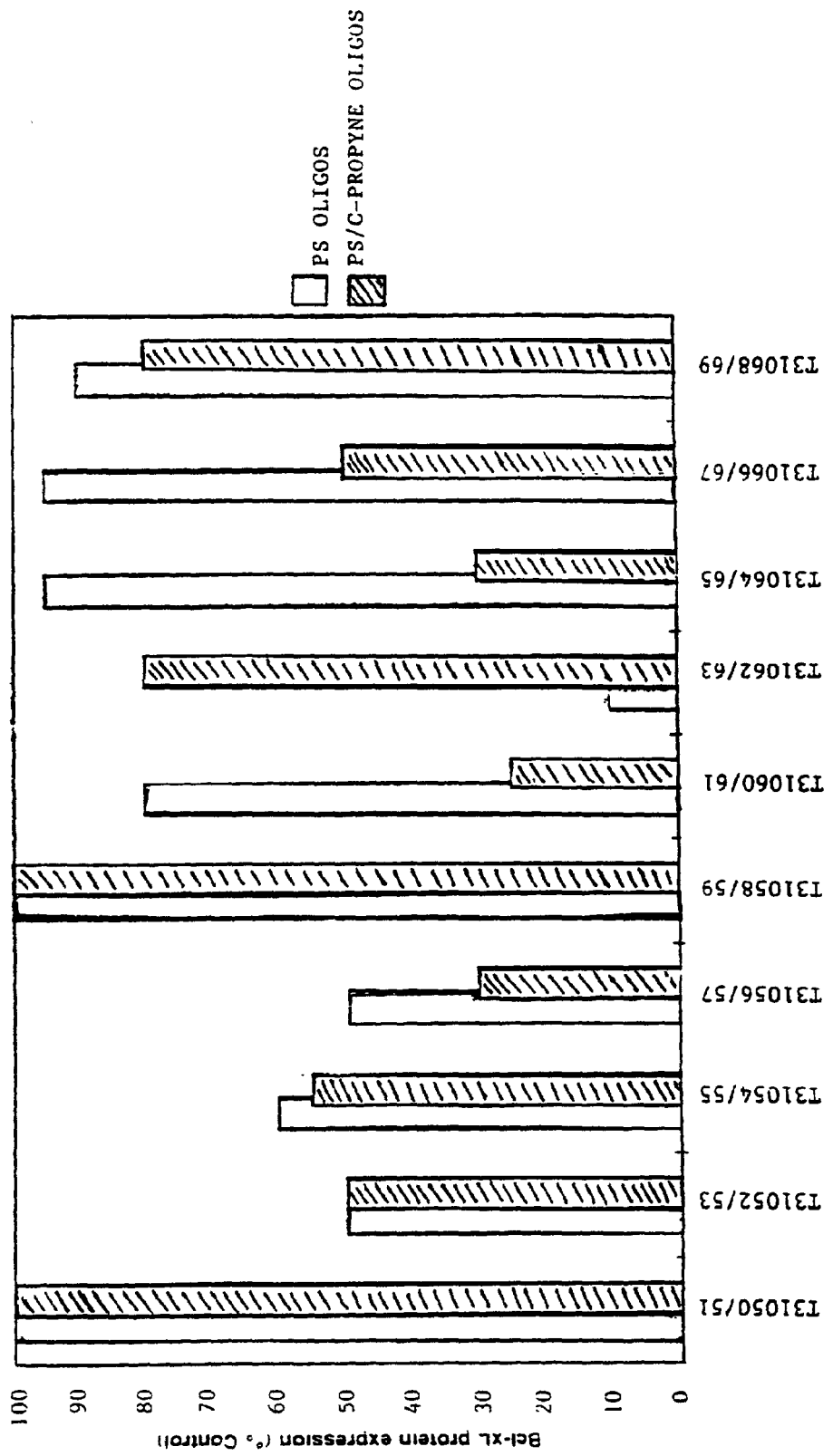
FIGURE 6  Effect of 18-mer PS oligonucleotides on bcl-xL protein expression in LNCaP cells LNCaP cell line Regulation of Bcl-Family Proteins with 2'-O-Methyl - Modified PS Oligonucleotides in T24 Cell Line Delivery: 1 uM oligo, 5 ug/ml Lipofectin

FIG. 10

The Most Active Chimeric PS-PO Oligonucleotides by
Their Ability to Down-Regulate Bcl-xL Protein Expression

| # | 5'- | | -3' |
|---|---|---|---|
| 29 | | C*T*C*aaC*CagT*C*CaT*C*CaT*gT*C*C*a | |
| 41 | | CT*g*C*gaT*C*CgaC*T*CaC*C*a*a*t | |
| 43 | | C*gC*C*gT*T*C*T*C*C*TggaTC*C*a*a | |
| 57 | | g*g*T*CT*C*CaT*CT*CCga*T*T*c | |
| 61 | | C*T*T*TaCTgC*TgC*CaT*g*g*g* | |
| 62 | | c*c*t* ggg gt g* atg* tgg* a*g*c | |
| 63 | | C*C*T* ggg gTg*aTg*tgg*a*g* | |

C, T - propynyl modified bases, * - PS

Regulation of Bcl-xL and Bax Proteins with 2'-O-Methyl-Modified PS Oligonucleotides in LNCaP Cell Line Delivery: 1 uM oligo, 5 uM An Down-Regulation of Bcl-Family Proteins Expression with PS-PO Oligonucleotides in LNCaP Cell Line Down-Regulation of Bcl-Family Proteins Expression with PS-PO Oligonucleotides in PC3 Cell Line Down-Regulation of Bcl-xL mRNA with PS-PO Oligonucleotides in T24 Cell Line

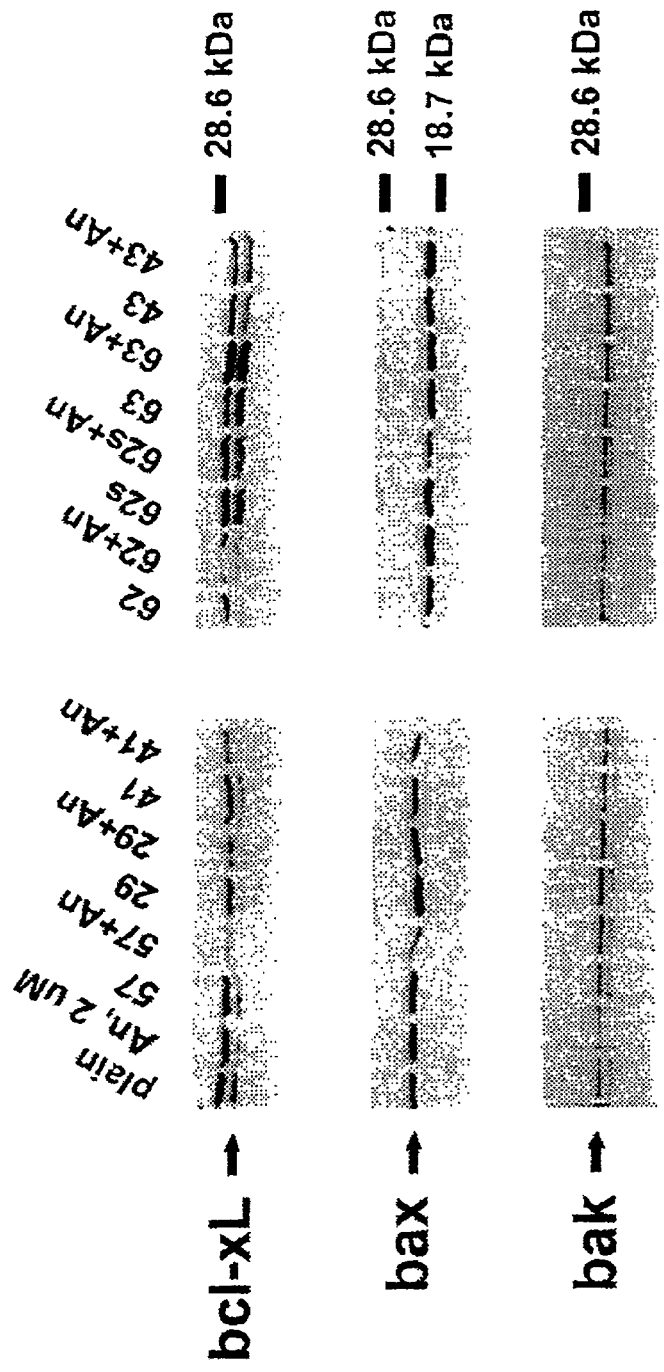
FIG. 17 Regulation of Bcl-Family Proteins with PS-PO Oligonucleotides in LNCaP Cell Line

SEQUENCE LISTING

```
<160> NUMBER OF SEQ ID NOS: 38

<210> SEQ ID NO 1
<211> LENGTH: 20
<212> TYPE: DNA
<213> ORGANISM: Artificial Sequence
<220> FEATURE:
<223> OTHER INFORMATION: ANTISENSE OLIGONUCLEOTIDE

<400> SEQUENCE: 1
ctcaaccagt ccattgtcca                                                   20

<210> SEQ ID NO 2
<211> LENGTH: 20
<212> TYPE: DNA
<213> ORGANISM: Artificial Sequence
<220> FEATURE:
<223> OTHER INFORMATION: ANTISENSE OLIGONUCLEOTIDE

<400> SEQUENCE: 2
tcccggttgc tctgagacat                                                   20

<210> SEQ ID NO 3
<211> LENGTH: 20
<212> TYPE: DNA
<213> ORGANISM: Artificial Sequence
<220> FEATURE:
<223> OTHER INFORMATION: ANTISENSE OLIGONUCLEOTIDE

<400> SEQUENCE: 3
gccacagtca tgcccgtcag                                                   20

<210> SEQ ID NO 4
<211> LENGTH: 20
<212> TYPE: DNA
<213> ORGANISM: Artificial Sequence
<220> FEATURE:
<223> OTHER INFORMATION: ANTISENSE OLIGONUCLEOTIDE

<400> SEQUENCE: 4
ctgcgatccg actcaccaat                                                   20

<210> SEQ ID NO 5
<211> LENGTH: 18
<212> TYPE: DNA
<213> ORGANISM: Artificial Sequence
<220> FEATURE:
<223> OTHER INFORMATION: ANTISENSE OLIGONUCLEOTIDE

<400> SEQUENCE: 5
agtcctgttc tcttccac                                                     18

<210> SEQ ID NO 6
<211> LENGTH: 18
<212> TYPE: DNA
<213> ORGANISM: Artificial Sequence
<220> FEATURE:
<223> OTHER INFORMATION: ANTISENSE OLIGONUCLEOTIDE

<400> SEQUENCE: 6
ctttactgct gccatggg                                                     18
```

```
<210> SEQ ID NO 7
<211> LENGTH: 20
<212> TYPE: DNA
<213> ORGANISM: Artificial Sequence
<220> FEATURE:
<223> OTHER INFORMATION: ANTISENSE OLIGONUCLEOTIDE

<400> SEQUENCE: 7
cgccgttctc ctggatccaa                                               20

<210> SEQ ID NO 8
<211> LENGTH: 18
<212> TYPE: DNA
<213> ORGANISM: Artificial Sequence
<220> FEATURE:
<223> OTHER INFORMATION: ANTISENSE OLIGONUCLEOTIDE

<400> SEQUENCE: 8
ctgactccag ctgtatcc                                                 18

<210> SEQ ID NO 9
<211> LENGTH: 18
<212> TYPE: DNA
<213> ORGANISM: Artificial Sequence
<220> FEATURE:
<223> OTHER INFORMATION: ANTISENSE OLIGONUCLEOTIDE

<400> SEQUENCE: 9
ggtctccatc tccgattc                                                 18

<210> SEQ ID NO 10
<211> LENGTH: 18
<212> TYPE: DNA
<213> ORGANISM: Artificial Sequence
<220> FEATURE:
<223> OTHER INFORMATION: ANTISENSE OLIGONUCLEOTIDE

<400> SEQUENCE: 10
cctggggtga tgtggagc                                                 18

<210> SEQ ID NO 11
<211> LENGTH: 18
<212> TYPE: DNA
<213> ORGANISM: Artificial Sequence
<220> FEATURE:
<223> OTHER INFORMATION: ANTISENSE OLIGONUCLEOTIDE

<400> SEQUENCE: 11
agttccacaa aagtatcc                                                 18

<210> SEQ ID NO 12
<211> LENGTH: 18
<212> TYPE: DNA
<213> ORGANISM: Artificial Sequence
<220> FEATURE:
<223> OTHER INFORMATION: ANTISENSE OLIGONUCLEOTIDE

<400> SEQUENCE: 12
ctttcggctc tcggctgc                                                 18

<210> SEQ ID NO 13
<211> LENGTH: 18
<212> TYPE: DNA
<213> ORGANISM: Artificial Sequence
<220> FEATURE:
```

```
<223> OTHER INFORMATION: ANTISENSE OLIGONUCLEOTIDE

<400> SEQUENCE: 13
aaccagcggt tgaagcgt                                              18

<210> SEQ ID NO 14
<211> LENGTH: 20
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(4)
<223> OTHER INFORMATION: PHOSPHOROTHIOATE LINKAGE
<220> FEATURE:
<221> NAME/KEY: misc_binding
<222> LOCATION: (6)..(7)
<223> OTHER INFORMATION: PHOSPHOROTHIOATE LINKAGE
<220> FEATURE:
<221> NAME/KEY: misc_binding
<222> LOCATION: (10)..(12)
<223> OTHER INFORMATION: PHOSPHOROTHIOATE LINKAGE
<220> FEATURE:
<221> NAME/KEY: misc_binding
<222> LOCATION: (14)..(15)
<223> OTHER INFORMATION: PHOSPHOROTHIOATE LINKAGE
<220> FEATURE:
<221> NAME/KEY: misc_binding
<222> LOCATION: (17)..(20)
<223> OTHER INFORMATION: PHOSPHOROTHIOATE LINKAGE

<400> SEQUENCE: 14
ctcaaccagt ccattgtcca                                            20

<210> SEQ ID NO 15
<211> LENGTH: 20
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(4)
<223> OTHER INFORMATION: PHOSPHOROTHIOATE LINKAGE
<220> FEATURE:
<221> NAME/KEY: misc_binding
<222> LOCATION: (6)..(7)
<223> OTHER INFORMATION: PHOSPHOROTHIOATE LINKAGE
<220> FEATURE:
<221> NAME/KEY: misc_binding
<222> LOCATION: (10)..(12)
<223> OTHER INFORMATION: PHOSPHOROTHIOATE LINKAGE
<220> FEATURE:
<221> NAME/KEY: misc_binding
<222> LOCATION: (14)..(15)
<223> OTHER INFORMATION: PHOSPHOROTHIOATE LINKAGE
<220> FEATURE:
<221> NAME/KEY: misc_binding
<222> LOCATION: (17)..(20)
<223> OTHER INFORMATION: PHOSPHOROTHIOATE LINKAGE
<220> FEATURE:
<221> NAME/KEY: modified_base
<222> LOCATION: (1)..(1)
<223> OTHER INFORMATION: PROPYNYL dC
<220> FEATURE:
<221> NAME/KEY: modified_base
<222> LOCATION: (2)..(2)
<223> OTHER INFORMATION: PROPYNYL dT
<220> FEATURE:
<221> NAME/KEY: modified_base
<222> LOCATION: (3)..(3)
<223> OTHER INFORMATION: PROPYNYL dC
<220> FEATURE:
<221> NAME/KEY: modified_base
```

```
<222> LOCATION: (6)..(6)
<223> OTHER INFORMATION: PROPYNYL dC
<220> FEATURE:
<221> NAME/KEY: modified_base
<222> LOCATION: (7)..(7)
<223> OTHER INFORMATION: PROPYNYL dC
<220> FEATURE:
<221> NAME/KEY: modified_base
<222> LOCATION: (10)..(10)
<223> OTHER INFORMATION: PROPYNYL dT
<220> FEATURE:
<221> NAME/KEY: modified_base
<222> LOCATION: (11)..(12)
<223> OTHER INFORMATION: PROPYNYL dC
<220> FEATURE:
<221> NAME/KEY: modified_base
<222> LOCATION: (14)..(15)
<223> OTHER INFORMATION: PROPYNYL dT
<220> FEATURE:
<221> NAME/KEY: modified_base
<222> LOCATION: (17)..(17)
<223> OTHER INFORMATION: PROPYNYL dT
<220> FEATURE:
<221> NAME/KEY: modified_base
<222> LOCATION: (18)..(19)
<223> OTHER INFORMATION: PROPYNYL dC

<400> SEQUENCE: 15
ctcaaccagt ccattgtcca                                               20

<210> SEQ ID NO 16
<211> LENGTH: 20
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(4)
<223> OTHER INFORMATION: PHOSPHOROTHIOATE   LINKAGE
<220> FEATURE:
<221> NAME/KEY: misc_binding
<222> LOCATION: (7)..(8)
<223> OTHER INFORMATION: PHOSPHOROTHIOATE   LINKAGE
<220> FEATURE:
<221> NAME/KEY: misc_binding
<222> LOCATION: (10)..(13)
<223> OTHER INFORMATION: PHOSPHOROTHIOATE   LINKAGE
<220> FEATURE:
<221> NAME/KEY: misc_binding
<222> LOCATION: (17)..(20)
<223> OTHER INFORMATION: PHOSPHOROTHIOATE   LINKAGE

<400> SEQUENCE: 16
tcccggttgc tctgagacat                                               20

<210> SEQ ID NO 17
<211> LENGTH: 20
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(4)
<223> OTHER INFORMATION: PHOSPHOROTHIOATE   LINKAGE
<220> FEATURE:
<221> NAME/KEY: misc_binding
<222> LOCATION: (8)..(9)
<223> OTHER INFORMATION: PHOSPHOROTHIOATE   LINKAGE
<220> FEATURE:
<221> NAME/KEY: misc_binding
<222> LOCATION: (13)..(15)
<223> OTHER INFORMATION: PHOSPHOROTHIOATE   LINKAGE
<220> FEATURE:
```

```
<221> NAME/KEY: misc_binding
<222> LOCATION: (17)..(20)
<223> OTHER INFORMATION: PHOSPHOROTHIOATE LINKAGE

<400> SEQUENCE: 17
gccacagtca tgcccgtcag                                          20

<210> SEQ ID NO 18
<211> LENGTH: 20
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(4)
<223> OTHER INFORMATION: PHOSPHOROTHIOATE LINKAGE
<220> FEATURE:
<221> NAME/KEY: modified_base
<222> LOCATION: (2)..(3)
<223> OTHER INFORMATION: PROPYNYL dC
<220> FEATURE:
<221> NAME/KEY: modified_base
<222> LOCATION: (5)..(5)
<223> OTHER INFORMATION: PROPYNYL dC
<220> FEATURE:
<221> NAME/KEY: modified_base
<222> LOCATION: (8)..(8)
<223> OTHER INFORMATION: PROPYNYL dT
<220> FEATURE:
<221> NAME/KEY: modified_base
<222> LOCATION: (9)..(9)
<223> OTHER INFORMATION: PROPYNYL dC
<220> FEATURE:
<221> NAME/KEY: modified_base
<222> LOCATION: (11)..(11)
<223> OTHER INFORMATION: PROPYNYL dT
<220> FEATURE:
<221> NAME/KEY: modified_base
<222> LOCATION: (13)..(15)
<223> OTHER INFORMATION: PROPYNYL dC
<220> FEATURE:
<221> NAME/KEY: modified_base
<222> LOCATION: (17)..(17)
<223> OTHER INFORMATION: PROPYNYL dT
<220> FEATURE:
<221> NAME/KEY: modified_base
<222> LOCATION: (18)..(18)
<223> OTHER INFORMATION: PROPYNYL dC
<220> FEATURE:
<221> NAME/KEY: misc_binding
<222> LOCATION: (8)..(9)
<223> OTHER INFORMATION: PHOSPHOROTHIOATE LINKAGE
<220> FEATURE:
<221> NAME/KEY: misc_binding
<222> LOCATION: (13)..(15)
<223> OTHER INFORMATION: PHOSPHOROTHIOATE LINKAGE
<220> FEATURE:
<221> NAME/KEY: misc_binding
<222> LOCATION: (17)..(20)
<223> OTHER INFORMATION: PHOSPHOROTHIOATE LINKAGE

<400> SEQUENCE: 18
gccacagtca tgcccgtcag                                          20

<210> SEQ ID NO 19
<211> LENGTH: 20
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (2)..(3)
<223> OTHER INFORMATION: PHOSPHOROTHIOATE LINKAGE
```

```
<220> FEATURE:
<221> NAME/KEY: misc_binding
<222> LOCATION: (7)..(9)
<223> OTHER INFORMATION: PHOSPHOROTHIOATE LINKAGE
<220> FEATURE:
<221> NAME/KEY: misc_binding
<222> LOCATION: (12)..(14)
<223> OTHER INFORMATION: PHOSPHOROTHIOATE LINKAGE
<220> FEATURE:
<221> NAME/KEY: misc_binding
<222> LOCATION: (16)..(20)
<223> OTHER INFORMATION: PHOSPHOROTHIOATE LINKAGE
<220> FEATURE:
<221> NAME/KEY: modified_base
<222> LOCATION: (1)..(1)
<223> OTHER INFORMATION: PROPYNYL dC
<220> FEATURE:
<221> NAME/KEY: modified_base
<222> LOCATION: (2)..(2)
<223> OTHER INFORMATION: PROPYNYL dT
<220> FEATURE:
<221> NAME/KEY: modified_base
<222> LOCATION: (4)..(4)
<223> OTHER INFORMATION: PROPYNYL dC
<220> FEATURE:
<221> NAME/KEY: modified_base
<222> LOCATION: (7)..(7)
<223> OTHER INFORMATION: PROPYNYL dT
<220> FEATURE:
<221> NAME/KEY: modified_base
<222> LOCATION: (8)..(9)
<223> OTHER INFORMATION: PROPYNYL dC
<220> FEATURE:
<221> NAME/KEY: modified_base
<222> LOCATION: (12)..(12)
<223> OTHER INFORMATION: PROPYNYL dC
<220> FEATURE:
<221> NAME/KEY: modified_base
<222> LOCATION: (13)..(13)
<223> OTHER INFORMATION: PROPYNYL dT
<220> FEATURE:
<221> NAME/KEY: modified_base
<222> LOCATION: (16)..(17)
<223> OTHER INFORMATION: PROPYNYL dC

<400> SEQUENCE: 19
ctgcgatccg actcaccaat                                              20

<210> SEQ ID NO 20
<211> LENGTH: 18
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(6)
<223> OTHER INFORMATION: PHOSPHOROTHIOATE LINKAGE
<220> FEATURE:
<221> NAME/KEY: misc_binding
<222> LOCATION: (8)..(9)
<223> OTHER INFORMATION: PHOSPHOROTHIOATE LINKAGE
<220> FEATURE:
<221> NAME/KEY: misc_binding
<222> LOCATION: (10)..(12)
<223> OTHER INFORMATION: PHOSPHOROTHIOATE LINKAGE
<220> FEATURE:
<221> NAME/KEY: misc_binding
<222> LOCATION: (13)..(18)
<223> OTHER INFORMATION: PHOSPHOROTHIOATE LINKAGE

<400> SEQUENCE: 20
agtcctgttc tcttccac                                                18

<210> SEQ ID NO 21
```

```
<211> LENGTH: 18
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(9)
<223> OTHER INFORMATION: PHOSPHOROTHIOATE LINKAGE
<220> FEATURE:
<221> NAME/KEY: misc_binding
<222> LOCATION: (10)..(12)
<223> OTHER INFORMATION: PHOSPHOROTHIOATE LINKAGE
<220> FEATURE:
<221> NAME/KEY: misc_binding
<222> LOCATION: (13)..(18)
<223> OTHER INFORMATION: PHOSPHOROTHIOATE LINKAGE
<220> FEATURE:
<221> NAME/KEY: modified_base
<222> LOCATION: (3)..(3)
<223> OTHER INFORMATION: PROPYNYL dT
<220> FEATURE:
<221> NAME/KEY: modified_base
<222> LOCATION: (4)..(6)
<223> OTHER INFORMATION: PROPYNYL dC
<220> FEATURE:
<221> NAME/KEY: modified_base
<222> LOCATION: (8)..(9)
<223> OTHER INFORMATION: PROPYNYL dT
<220> FEATURE:
<221> NAME/KEY: modified_base
<222> LOCATION: (10)..(10)
<223> OTHER INFORMATION: PROPYNYL dC
<220> FEATURE:
<221> NAME/KEY: modified_base
<222> LOCATION: (11)..(11)
<223> OTHER INFORMATION: PROPYNYL dT
<220> FEATURE:
<221> NAME/KEY: modified_base
<222> LOCATION: (12)..(12)
<223> OTHER INFORMATION: PROPYNYL dC
<220> FEATURE:
<221> NAME/KEY: modified_base
<222> LOCATION: (13)..(14)
<223> OTHER INFORMATION: PROPYNYL dT
<220> FEATURE:
<221> NAME/KEY: modified_base
<222> LOCATION: (15)..(16)
<223> OTHER INFORMATION: PROPYNYL dC

<400> SEQUENCE: 21
agtcccgttc tcttccac                                               18

<210> SEQ ID NO 22
<211> LENGTH: 18
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(4)
<223> OTHER INFORMATION: PHOSPHOROTHIOATE LINKAGE
<220> FEATURE:
<221> NAME/KEY: misc_binding
<222> LOCATION: (9)..(10)
<223> OTHER INFORMATION: PHOSPHOROTHIOATE LINKAGE
<220> FEATURE:
<221> NAME/KEY: misc_binding
<222> LOCATION: (12)..(13)
<223> OTHER INFORMATION: PHOSPHOROTHIOATE LINKAGE
<220> FEATURE:
<221> NAME/KEY: misc_binding
<222> LOCATION: (15)..(18)
<223> OTHER INFORMATION: PHOSPHOROTHIOATE LINKAGE
<220> FEATURE:
<221> NAME/KEY: modified_base
```

```
<222> LOCATION: (1)..(1)
<223> OTHER INFORMATION: PROPYNYL dC
<220> FEATURE:
<221> NAME/KEY: modified_base
<222> LOCATION: (2)..(4)
<223> OTHER INFORMATION: PROPYNYL dT
<220> FEATURE:
<221> NAME/KEY: modified_base
<222> LOCATION: (6)..(6)
<223> OTHER INFORMATION: PROPYNYL dC
<220> FEATURE:
<221> NAME/KEY: modified_base
<222> LOCATION: (7)..(7)
<223> OTHER INFORMATION: PROPYNYL dT
<220> FEATURE:
<221> NAME/KEY: modified_base
<222> LOCATION: (9)..(9)
<223> OTHER INFORMATION: PROPYNYL dC
<220> FEATURE:
<221> NAME/KEY: modified_base
<222> LOCATION: (10)..(10)
<223> OTHER INFORMATION: PROPYNYL dT
<220> FEATURE:
<221> NAME/KEY: modified_base
<222> LOCATION: (12)..(13)
<223> OTHER INFORMATION: PROPYNYL dC
<220> FEATURE:
<221> NAME/KEY: modified_base
<222> LOCATION: (15)..(15)
<223> OTHER INFORMATION: PROPYNYL dT

<400> SEQUENCE: 22
ctttactgct gccatggg                                                 18

<210> SEQ ID NO 23
<211> LENGTH: 20
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(2)
<223> OTHER INFORMATION: PHOSPHOROTHIOATE LINKAGE
<220> FEATURE:
<221> NAME/KEY: misc_binding
<222> LOCATION: (3)..(5)
<223> OTHER INFORMATION: PHOSPHOROTHIOATE LINKAGE
<220> FEATURE:
<221> NAME/KEY: misc_binding
<222> LOCATION: (6)..(12)
<223> OTHER INFORMATION: PHOSPHOROTHIOATE LINKAGE
<220> FEATURE:
<221> NAME/KEY: misc_binding
<222> LOCATION: (17)..(20)
<223> OTHER INFORMATION: PHOSPHOROTHIOATE LINKAGE
<220> FEATURE:
<221> NAME/KEY: modified_base
<222> LOCATION: (1)..(1)
<223> OTHER INFORMATION: PROPYNYL dC
<220> FEATURE:
<221> NAME/KEY: modified_base
<222> LOCATION: (3)..(4)
<223> OTHER INFORMATION: PROPYNYL dC
<220> FEATURE:
<221> NAME/KEY: modified_base
<222> LOCATION: (8)..(8)
<223> OTHER INFORMATION: PROPYNYL dC
<220> FEATURE:
<221> NAME/KEY: modified_base
<222> LOCATION: (10)..(11)
<223> OTHER INFORMATION: PROPYNYL dC
<220> FEATURE:
<221> NAME/KEY: modified_base
<222> LOCATION: (17)..(18)
<223> OTHER INFORMATION: PROPYNYL dC
<220> FEATURE:
```

```
<221> NAME/KEY: modified_base
<222> LOCATION: (6)..(7)
<223> OTHER INFORMATION: PROPYNYL dT
<220> FEATURE:
<221> NAME/KEY: modified_base
<222> LOCATION: (12)..(12)
<223> OTHER INFORMATION: PROPYNYL dT
<220> FEATURE:
<221> NAME/KEY: modified_base
<222> LOCATION: (16)..(16)
<223> OTHER INFORMATION: PROPYNYL dT
<220> FEATURE:
<221> NAME/KEY: modified_base
<222> LOCATION: (9)..(9)
<223> OTHER INFORMATION: PROPYNYL dT

<400> SEQUENCE: 23
cgccgttctc ctggatccaa                                               20

<210> SEQ ID NO 24
<211> LENGTH: 19
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(2)
<223> OTHER INFORMATION: PHOSPHOROTHIOATE LINKAGE
<220> FEATURE:
<221> NAME/KEY: misc_binding
<222> LOCATION: (3)..(5)
<223> OTHER INFORMATION: PHOSPHOROTHIOATE LINKAGE
<220> FEATURE:
<221> NAME/KEY: misc_binding
<222> LOCATION: (6)..(12)
<223> OTHER INFORMATION: PHOSPHOROTHIOATE LINKAGE
<220> FEATURE:
<221> NAME/KEY: misc_binding
<222> LOCATION: (17)..(19)
<223> OTHER INFORMATION: PHOSPHOROTHIOATE LINKAGE

<400> SEQUENCE: 24
cgccgttctc ctggatcca                                                19

<210> SEQ ID NO 25
<211> LENGTH: 18
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(4)
<223> OTHER INFORMATION: PHOSPHOROTHIOATE LINKAGE
<220> FEATURE:
<221> NAME/KEY: misc_binding
<222> LOCATION: (5)..(8)
<223> OTHER INFORMATION: PHOSPHOROTHIOATE LINKAGE
<220> FEATURE:
<221> NAME/KEY: misc_binding
<222> LOCATION: (11)..(12)
<223> OTHER INFORMATION: PHOSPHOROTHIOATE LINKAGE
<220> FEATURE:
<221> NAME/KEY: misc_binding
<222> LOCATION: (15)..(18)
<223> OTHER INFORMATION: PHOSPHOROTHIOATE LINKAGE
<220> FEATURE:
<221> NAME/KEY: modified_base
<222> LOCATION: (1)..(1)
<223> OTHER INFORMATION: PROPYNYL dC
<220> FEATURE:
<221> NAME/KEY: modified_base
<222> LOCATION: (2)..(2)
<223> OTHER INFORMATION: PROPYNYL dT
```

```
<220> FEATURE:
<221> NAME/KEY: modified_base
<222> LOCATION: (5)..(5)
<223> OTHER INFORMATION: PROPYNYL dC
<220> FEATURE:
<221> NAME/KEY: modified_base
<222> LOCATION: (6)..(6)
<223> OTHER INFORMATION: PROPYNYL dT
<220> FEATURE:
<221> NAME/KEY: modified_base
<222> LOCATION: (7)..(8)
<223> OTHER INFORMATION: PROPYNYL dC
<220> FEATURE:
<221> NAME/KEY: modified_base
<222> LOCATION: (11)..(11)
<223> OTHER INFORMATION: PROPYNYL dC
<220> FEATURE:
<221> NAME/KEY: modified_base
<222> LOCATION: (12)..(12)
<223> OTHER INFORMATION: PROPYNYL dT
<220> FEATURE:
<221> NAME/KEY: modified_base
<222> LOCATION: (14)..(14)
<223> OTHER INFORMATION: PROPYNYL dT
<220> FEATURE:
<221> NAME/KEY: modified_base
<222> LOCATION: (16)..(16)
<223> OTHER INFORMATION: PROPYNYL dT
<220> FEATURE:
<221> NAME/KEY: modified_base
<222> LOCATION: (17)..(17)
<223> OTHER INFORMATION: PROPYNYL dC

<400> SEQUENCE: 25
ctgactccag ctgtatcc                                              18

<210> SEQ ID NO 26
<211> LENGTH: 18
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(4)
<223> OTHER INFORMATION: PHOSPHOROTHIOATE LINKAGE
<220> FEATURE:
<221> NAME/KEY: misc_binding
<222> LOCATION: (5)..(8)
<223> OTHER INFORMATION: PHOSPHOROTHIOATE LINKAGE
<220> FEATURE:
<221> NAME/KEY: misc_binding
<222> LOCATION: (11)..(12)
<223> OTHER INFORMATION: PHOSPHOROTHIOATE LINKAGE
<220> FEATURE:
<221> NAME/KEY: misc_binding
<222> LOCATION: (15)..(18)
<223> OTHER INFORMATION: PHOSPHOROTHIOATE LINKAGE

<400> SEQUENCE: 26
ctgactccag ctgtatcc                                              18

<210> SEQ ID NO 27
<211> LENGTH: 18
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(4)
<223> OTHER INFORMATION: PHOSPHOROTHIATE LINKAGE
<220> FEATURE:
<221> NAME/KEY: misc_binding
<222> LOCATION: (5)..(7)
```

```
<223> OTHER INFORMATION: PHOSPHOROTHIATE LINKAGE
<220> FEATURE:
<221> NAME/KEY: misc_binding
<222> LOCATION: (9)..(10)
<223> OTHER INFORMATION: PHOSPHOROTHIATE LINKAGE
<220> FEATURE:
<221> NAME/KEY: misc_binding
<222> LOCATION: (11)..(12)
<223> OTHER INFORMATION: PHOSPHOROTHIATE LINKAGE
<220> FEATURE:
<221> NAME/KEY: misc_binding
<222> LOCATION: (15)..(18)
<223> OTHER INFORMATION: PHOSPHOROTHIATE LINKAGE
<220> FEATURE:
<221> NAME/KEY: modified_base
<222> LOCATION: (3)..(3)
<223> OTHER INFORMATION: PROPYNYL dT
<220> FEATURE:
<221> NAME/KEY: modified_base
<222> LOCATION: (4)..(4)
<223> OTHER INFORMATION: PROPYNYL dC
<220> FEATURE:
<221> NAME/KEY: modified_base
<222> LOCATION: (6)..(7)
<223> OTHER INFORMATION: PROPYNYL dC
<220> FEATURE:
<221> NAME/KEY: modified_base
<222> LOCATION: (5)..(5)
<223> OTHER INFORMATION: PROPYNYL dT
<220> FEATURE:
<221> NAME/KEY: modified_base
<222> LOCATION: (9)..(9)
<223> OTHER INFORMATION: PROPYNYL dT
<220> FEATURE:
<221> NAME/KEY: modified_base
<222> LOCATION: (10)..(10)
<223> OTHER INFORMATION: PROPYNYL dC
<220> FEATURE:
<221> NAME/KEY: modified_base
<222> LOCATION: (11)..(11)
<223> OTHER INFORMATION: PROPYNYL dT
<220> FEATURE:
<221> NAME/KEY: modified_base
<222> LOCATION: (12)..(13)
<223> OTHER INFORMATION: PROPYNYL dC
<220> FEATURE:
<221> NAME/KEY: modified_base
<222> LOCATION: (16)..(17)
<223> OTHER INFORMATION: PROPYNYL dT

<400> SEQUENCE: 27
ggtctccatc tccgattc                                                18

<210> SEQ ID NO 28
<211> LENGTH: 18
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(4)
<223> OTHER INFORMATION: PHOSPHOROTHIOATE LINKAGE
<220> FEATURE:
<221> NAME/KEY: misc_binding
<222> LOCATION: (5)..(7)
<223> OTHER INFORMATION: PHOSPHOROTHIOATE LINKAGE
<220> FEATURE:
<221> NAME/KEY: misc_binding
<222> LOCATION: (9)..(10)
<223> OTHER INFORMATION: PHOSPHOROTHIOATE LINKAGE
<220> FEATURE:
<221> NAME/KEY: misc_binding
<222> LOCATION: (11)..(12)
<223> OTHER INFORMATION: PHOSPHOROTHIOATE LINKAGE
<220> FEATURE:
<221> NAME/KEY: misc_binding
```

```
<222> LOCATION: (15)..(18)
<223> OTHER INFORMATION: PHOSPHOROTHIOATE LINKAGE

<400> SEQUENCE: 28
ggtctccatc tccgattc                                                 18

<210> SEQ ID NO 29
<211> LENGTH: 18
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(4)
<223> OTHER INFORMATION: PHOSPHOROTHIATE LINKAGE
<220> FEATURE:
<221> NAME/KEY: misc_binding
<222> LOCATION: (9)..(10)
<223> OTHER INFORMATION: PHOSPHOROTHIATE LINKAGE
<220> FEATURE:
<221> NAME/KEY: misc_binding
<222> LOCATION: (12)..(13)
<223> OTHER INFORMATION: PHOSPHOROTHIATE LINKAGE
<220> FEATURE:
<221> NAME/KEY: misc_binding
<222> LOCATION: (15)..(18)
<223> OTHER INFORMATION: PHOSPHOROTHIATE LINKAGE

<400> SEQUENCE: 29
cctggggtga tgtggagc                                                 18

<210> SEQ ID NO 30
<211> LENGTH: 18
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(4)
<223> OTHER INFORMATION: PHOSPHOROTHIOATE LINKAGE
<220> FEATURE:
<221> NAME/KEY: misc_binding
<222> LOCATION: (5)..(6)
<223> OTHER INFORMATION: PHOSPHOROTHIOATE LINKAGE
<220> FEATURE:
<221> NAME/KEY: misc_binding
<222> LOCATION: (8)..(9)
<223> OTHER INFORMATION: PHOSPHOROTHIOATE LINKAGE
<220> FEATURE:
<221> NAME/KEY: misc_binding
<222> LOCATION: (14)..(18)
<223> OTHER INFORMATION: PHOSPHOROTHIOATE LINKAGE
<220> FEATURE:
<221> NAME/KEY: modified_base
<222> LOCATION: (3)..(4)
<223> OTHER INFORMATION: PROPYNYL dT
<220> FEATURE:
<221> NAME/KEY: modified_base
<222> LOCATION: (5)..(6)
<223> OTHER INFORMATION: PROPYNYL dC
<220> FEATURE:
<221> NAME/KEY: modified_base
<222> LOCATION: (8)..(8)
<223> OTHER INFORMATION: PROPYNYL dC
<220> FEATURE:
<221> NAME/KEY: modified_base
<222> LOCATION: (14)..(14)
<223> OTHER INFORMATION: PROPYNYL dT
<220> FEATURE:
<221> NAME/KEY: modified_base
<222> LOCATION: (16)..(16)
<223> OTHER INFORMATION: PROPYNYL dT
<220> FEATURE:
```

```
<221> NAME/KEY: modified_base
<222> LOCATION: (17)..(17)
<223> OTHER INFORMATION: PROPYNYL dC

<400> SEQUENCE: 30
agttccacaa aagtatcc                                                    18

<210> SEQ ID NO 31
<211> LENGTH: 18
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(4)
<223> OTHER INFORMATION: PHOSPHOROTHIOATE LINKAGE
<220> FEATURE:
<221> NAME/KEY: misc_binding
<222> LOCATION: (5)..(6)
<223> OTHER INFORMATION: PHOSPHOROTHIOATE LINKAGE
<220> FEATURE:
<221> NAME/KEY: misc_binding
<222> LOCATION: (8)..(9)
<223> OTHER INFORMATION: PHOSPHOROTHIOATE LINKAGE
<220> FEATURE:
<221> NAME/KEY: misc_binding
<222> LOCATION: (14)..(18)
<223> OTHER INFORMATION: PHOSPHOROTHIOATE LINKAGE

<400> SEQUENCE: 31
agttccacaa aagtatcc                                                    18

<210> SEQ ID NO 32
<211> LENGTH: 18
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(4)
<223> OTHER INFORMATION: PHOSPHOROTHIOATE LINKAGE
<220> FEATURE:
<221> NAME/KEY: misc_binding
<222> LOCATION: (8)..(9)
<223> OTHER INFORMATION: PHOSPHOROTHIOATE LINKAGE
<220> FEATURE:
<221> NAME/KEY: misc_binding
<222> LOCATION: (10)..(12)
<223> OTHER INFORMATION: PHOSPHOROTHIOATE LINKAGE
<220> FEATURE:
<221> NAME/KEY: misc_binding
<222> LOCATION: (15)..(18)
<223> OTHER INFORMATION: PHOSPHOROTHIOATE LINKAGE
<220> FEATURE:
<221> NAME/KEY: modified_base
<222> LOCATION: (1)..(1)
<223> OTHER INFORMATION: PROPYNYL dC
<220> FEATURE:
<221> NAME/KEY: modified_base
<222> LOCATION: (2)..(4)
<223> OTHER INFORMATION: PROPYNYL dT
<220> FEATURE:
<221> NAME/KEY: modified_base
<222> LOCATION: (8)..(8)
<223> OTHER INFORMATION: PROPYNYL dC
<220> FEATURE:
<221> NAME/KEY: modified_base
<222> LOCATION: (9)..(9)
<223> OTHER INFORMATION: PROPYNYL dT
<220> FEATURE:
<221> NAME/KEY: modified_base
<222> LOCATION: (10)..(10)
<223> OTHER INFORMATION: PROPYNYL dC
```

```
<220> FEATURE:
<221> NAME/KEY: modified_base
<222> LOCATION: (11)..(11)
<223> OTHER INFORMATION: PROPYNYL dT
<220> FEATURE:
<221> NAME/KEY: modified_base
<222> LOCATION: (12)..(12)
<223> OTHER INFORMATION: PROPYNYL dC
<220> FEATURE:
<221> NAME/KEY: modified_base
<222> LOCATION: (15)..(15)
<223> OTHER INFORMATION: PROPYNYL dC
<220> FEATURE:
<221> NAME/KEY: modified_base
<222> LOCATION: (16)..(16)
<223> OTHER INFORMATION: PROPYNYL dT

<400> SEQUENCE: 32
ctttcggctc tcggctgc                                                 18

<210> SEQ ID NO 33
<211> LENGTH: 18
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(4)
<223> OTHER INFORMATION: PHOSPHOROTHIOATE LINKAGE
<220> FEATURE:
<221> NAME/KEY: misc_binding
<222> LOCATION: (8)..(9)
<223> OTHER INFORMATION: PHOSPHOROTHIOATE LINKAGE
<220> FEATURE:
<221> NAME/KEY: misc_binding
<222> LOCATION: (10)..(12)
<223> OTHER INFORMATION: PHOSPHOROTHIOATE LINKAGE
<220> FEATURE:
<221> NAME/KEY: misc_binding
<222> LOCATION: (15)..(18)
<223> OTHER INFORMATION: PHOSPHOROTHIOATE LINKAGE

<400> SEQUENCE: 33
ctttcggctc tcggctgc                                                 18

<210> SEQ ID NO 34
<211> LENGTH: 18
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(4)
<223> OTHER INFORMATION: PHOSPHOROTHIOATE LINKAGE
<220> FEATURE:
<221> NAME/KEY: misc_binding
<222> LOCATION: (10)..(11)
<223> OTHER INFORMATION: PHOSPHOROTHIOATE LINKAGE
<220> FEATURE:
<221> NAME/KEY: misc_binding
<222> LOCATION: (15)..(18)
<223> OTHER INFORMATION: PHOSPHOROTHIOATE LINKAGE
<220> FEATURE:
<221> NAME/KEY: modified_base
<222> LOCATION: (3)..(4)
<223> OTHER INFORMATION: PROPYNYL dC
<220> FEATURE:
<221> NAME/KEY: modified_base
<222> LOCATION: (7)..(7)
<223> OTHER INFORMATION: PROPYNYL dC
<220> FEATURE:
<221> NAME/KEY: modified_base
<222> LOCATION: (16)..(16)
```

<223> OTHER INFORMATION: PROPYNYL dC

<400> SEQUENCE: 34
aaccagcggt tgaagcgt                                                  18

<210> SEQ ID NO 35
<211> LENGTH: 18
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(4)
<223> OTHER INFORMATION: PHOSPHOROTHIOATE LINKAGE
<220> FEATURE:
<221> NAME/KEY: misc_binding
<222> LOCATION: (10)..(12)
<223> OTHER INFORMATION: PHOSPHOROTHIOATE LINKAGE
<220> FEATURE:
<221> NAME/KEY: misc_binding
<222> LOCATION: (15)..(18)
<223> OTHER INFORMATION: PHOSPHOROTHIOATE LINKAGE

<400> SEQUENCE: 35
aaccagcggt tgaagcgt                                                  18

<210> SEQ ID NO 36
<211> LENGTH: 20
<212> TYPE: DNA
<213> ORGANISM: Artificial Sequence
<220> FEATURE:
<223> OTHER INFORMATION: PRIMER

<400> SEQUENCE: 36
atgtctcaga gcaaccggga                                                20

<210> SEQ ID NO 37
<211> LENGTH: 20
<212> TYPE: DNA
<213> ORGANISM: Artificial Sequence
<220> FEATURE:
<223> OTHER INFORMATION: PRIMER

<400> SEQUENCE: 37
tcatttccga ctgaagagtg                                                20

<210> SEQ ID NO 38
<211> LENGTH: 18
<212> TYPE: DNA
<213> ORGANISM: Artificial Sequence
<220> FEATURE:
<223> OTHER INFORMATION: ANTISENSE OLIGONUCLEOTIDE
<220> FEATURE:
<221> NAME/KEY: misc_binding
<222> LOCATION: (1)..(2)
<223> OTHER INFORMATION: PHOSPHOROTHIOATE LINKAGE
<220> FEATURE:
<221> NAME/KEY: misc_binding
<222> LOCATION: (2)..(3)
<223> OTHER INFORMATION: PHOSPHOROTHIOATE LINKAGE
<220> FEATURE:
<221> NAME/KEY: misc_binding
<222> LOCATION: (3)..(4)
<223> OTHER INFORMATION: PHOSPHOROTHIOATE LINKAGE
<220> FEATURE:
<221> NAME/KEY: misc_binding
<222> LOCATION: (9)..(10)
<223> OTHER INFORMATION: PHOSPHOROTHIOATE LINKAGE
<220> FEATURE:
<221> NAME/KEY: misc_binding

```
-continued

<222> LOCATION: (12)..(13)
<223> OTHER INFORMATION: PHOSPHOROTHIOATE LINKAGE
<220> FEATURE:
<221> NAME/KEY: misc_binding
<222> LOCATION: (15)..(16)
<223> OTHER INFORMATION: PHOSPHOROTHIOATE LINKAGE
<220> FEATURE:
<221> NAME/KEY: misc_binding
<222> LOCATION: (16)..(17)
<223> OTHER INFORMATION: PHOSPHOROTHIOATE LINKAGE
<220> FEATURE:
<221> NAME/KEY: modified_base
<222> LOCATION: (1)..(1)
<223> OTHER INFORMATION: PROPYNYL dC
<220> FEATURE:
<221> NAME/KEY: modified_base
<222> LOCATION: (2)..(2)
<223> OTHER INFORMATION: PROPYNYL dC
<220> FEATURE:
<221> NAME/KEY: modified_base
<222> LOCATION: (3)..(3)
<223> OTHER INFORMATION: PROPYNYL dT
<220> FEATURE:
<221> NAME/KEY: modified_base
<222> LOCATION: (8)..(8)
<223> OTHER INFORMATION: PROPYNYL dT
<220> FEATURE:
<221> NAME/KEY: modified_base
<222> LOCATION: (11)..(11)
<223> OTHER INFORMATION: PROPYNYL dT

<400> SEQUENCE: 38 cctgggtga tgtggagc                                                    18
```

US 7,074,769 B2

OLIGONUCLEOTIDE INHIBITORS OF BCL-XL

This application is a continuation of PCT International Application No. PCT/US99/15250, filed 2 Jul. 1999, designating the United States of America, which is a continuation-in-part of U.S. Ser. No. 09/109,614, filed Jul. 2, 1998, now abandoned, the contents of which are hereby incorporated by reference into the present application.

Throughout this application, various references are referred to. Disclosures of these publications in their entireties are hereby incorporated by reference into this application to more fully describe the state of the art to which this invention pertains.

BACKGROUND OF THE INVENTION

Bcl-xL is an important anti-apoptotic protein that belongs to the bcl-2 family. Bcl-xL is a critical determinant of intimal lesion formation and thus is an important contributor to the progression of vascular disease. Pollman et al. (1998) Nature Medicine 4: 222–227. In addition, bcl-xL has been implicated as a causative factor in cancer.

The subject invention involves oligonucleotides that reduce or eliminate the expression of bcl-xL. Synthetic oligodeoxynucleotides have been utilized as antisense inhibitors of mRNA translation in vitro and in vivo. Beaucage, S., and Caruthers, M., (1981) Tetrahedron Lett. 37:3557; Iverson, P. (1991) Anti-Cancer Drug Des. 6:531; Ratajczak, et al. (1992) Proc. Natl. Acad. Sci. U.S.A. 89:11823; Uhlmann, E., and Peyman, A. (1990) Chem. Rev. 90:544–579. Antisense oligonucleotides have found widespread application because of their abilities to control and/or inhibit gene expression in a selective manner in cellular systems. Ghosh, S., et al. (1990) J. Biol. Chem. 265: 2935–2940; Hemken, P., et al. (1992) J. Biol. Chem. 267: 9948–0057; Lestinger, R., U.S. Pat. No. 4,958,103, issued Sep. 18, 1990; Shewmaker et al., U.S. Pat. No. 5,107,065, issued Apr. 21, 1992; Tullis, U.S. Patent No., issued Jun. 11, 1991; Zhao, Q., et al. (1993) Antisense Research and Development 3:53–66. Thus, the subject invention represents a precise and selective way of regulating bcl-xl expression both in vivo and in vitro.

SUMMARY OF THE INVENTION

This invention provides an antisense oligonucleotide or analog thereof comprising 10 or more contiguous bases or base analogs from the sequence of bases of sequence A, B, C, D, E, F, G, H, I, J, K, L, or M of FIG. 1.

This invention also provides the above-described antisense oligonucleotides, wherein the nucleotide sequence comprises nucleotide sequence A, A', B, C, C', D, E, E', F, G, G', H, H', I, I', J, K, K', L, L', M, or M' of FIGS. 2A and 2B.

This invention also provides the above-described antisense oligonucleotides, wherein the oligonucleotide is encapsulated in a liposome or nanoparticle.

This invention also provides the above-described antisense oligonucleotides, wherein the phosphate backbone comprises phosphorothioate bonds.

In addition, this invention provides a method of treating cancer, comprising introducing into a tumor cell an effective amount of the the above-described antisense oligonucleotide, thereby reducing the levels of bcl-xL protein produced and treating cancer.

This invention further provides a method of treating cancer, comprising introducing into a tumor cell an effective amount of the the above-described antisense oligonucleotide, thereby reducing the levels of bcl-2 protein produced and treating cancer.

This invention also provides the above-described methods, wherein the introducing comprises using amine and cationic delivery reagents.

This invention also provides the above-described methods, wherein the introducing comprises using porphyrin or lipofectin as a delivery agent.

This invention further provides the above-described pharmaceutical compositions, wherein the pharmaceutical composition comprises tetra meso-(4-methylpyridyl)porphine or tetra meso-(anilinium)porphine or a combination thereof.

BRIEF DESCRIPTION OF THE FIGURES

FIG. 1

Figure 3D:
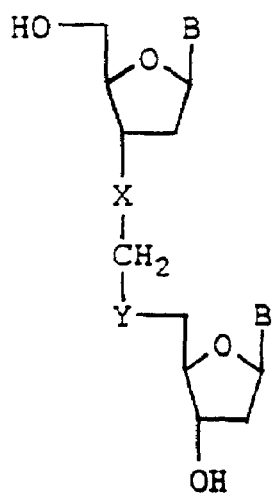

Oligonucleotide sequences complementary to bcl-$X_L$ mRNA; A (SEQ ID NO:1), B (SEQ ID NO:2), C (SEQ ID NO:3), D (SEQ ID NO:4), E (SEQ ID NO:5), F (SEQ ID NO:6), G (SEQ ID NO:7), H (SEQ ID NO:8), I (SEQ ID NO:9), J (SEQ ID NO:10), K (SEQ ID NO:11), L (SEQ ID NO:12), M (SEQ ID NO:13).

FIGS. 2A and 2B

Oligonucleotide sequences and analogs thereof complementary to bcl-$X_L$ mRNA; FIG. 2A shows: A (SEQ ID NO:14), A' (SEQ ID NO:15), B (SEQ ID NO:16), C (SEQ ID NO:17), C' (SEQ ID NO:18), D (SEQ ID NO:19), E (SEQ ID NO:20), E' (SEQ ID 21), F (SEQ ID NO:22), G (SEQ ID NO:23), G' (SEQ ID NO:24); FIG. 2B shows, H (SEQ ID NO:25), H' (SEQ ID NO:26), I (SEQ ID NO:27), I' (SEQ ID NO:28), J (SEQ ID NO:29), K (SEQ ID NO:30), K' (SEQ ID NO:31), L (SEQ ID NO:32), L' (SEQ ID NO:33), M (SEQ ID NO:34), M' (SEQ ID NO:35).

FIGS. 3A, 3B, 3C, and 3D

Some of the many possible phosphodiester moiety analogs.

FIG. 4

An example of a sugar containing an aminoalkyloxy linker.

FIGS. 5A and 5B

Some of the many possible base moiety analogs.

FIG. 6

Effect of 18-mer PS oligonucleotides on bcl-xL protein expression in LNCaP cells. The height of columns represents oligonucleotide inhibition of bcl-xL protein expression. Oligonucleotides were added to cells at a concentration of 1 µM in the presence of 3 µM of TAP for 4 h. The most active compound was T31062.

FIG. 7

Western blot analysis of bcl-xL protein expression in prostate cancer cell lines after oligonucleotide treatment. The treatment of the cell with complex of oligonucleotides T31057, T31061, T31062 (1 µM) with TMP (2 µM) or TAP (3 µM) down-regulates bcl-xL protein expression, whereas oligonucleotides alone do not cause this effect.

FIG. 8

Antisense Oligo nucleotides to Bcl-xL mRNA

FIG. 9

Regulation of Bcl-Family Proteins with 2"-O-Methyl—Modified PS Oligonucleotides in T24 Cell Line

FIG. 10

Most active chimeric PS-PO oligonucleotides by their ability to down-regulate Bcl-XL protein expression (from top to bottom SEQ ID NO:15; SEQ ID NO:19; SEQ ID NO:24; SEQ ID NO:27; SEQ ID NO:22; SEQ ID NO:29; and SEQ ID NO:38).

FIG. 11

Regulation of Bcl-family proteins with 2'-O-Methyl-Modified PS Oligonucleotides in PC-3 Cell Line

FIG. 12

Regulation of Bcl-xL and Bax proteins with 2'-O-Methyl-Modified PS oligonucleotides in LNCaP Cell Line

FIG. 13

Down-regulation of Bcl-family proteins expression with PS-PO oligonucleotides in LNCaP cell line

FIG. 14

Down-regulation of Bcl-family proteins expression with PS-PO oligonucleotides in PC3 cell line

FIG. 15

Regulation of Bcl-Family Proteins with PS-PO oligonucleotides in T24 Cell line

FIG. 16

Down-regulation of Bcl-xL mRNA with aPS-PO oligonucleotides in T24 cell line

FIG. 17

Regulation of Bcl-Family Proteins with PS-PO oligonucleotides in LNCaP cell line

DETAILED DESCRIPTION OF THE INVENTION

The following standard abbreviations are used throughout the specification to indicate specific nucleotides:

| C = Cytidine | A = Adenosine |
|---|---|
| T = Thymidine | G = Guanosine |

Nucleic acid synthesizers are available to synthesize oligonucleotides of any desired sequence. Certain oligonucleotide analogs may also be readily synthesized by modifying the reactants and reaction conditions. For example, phosphorothioate and methylphosphonate oligonucleotides may be synthesized using commercially available automated oligonucleotide synthesizers.

An oligonucleotide's binding affinity to a complementary nucleic acid may be assessed by determining the melting tempature ($T_M$) of a hybridization complex. The $T_M$ is a measure of the temperature required to separate the nucleic acid strands of a hybridization complex. The $T_M$ may be measured by using the hybridization complex's UV spectrum to assess the degree and strength of hybridization. During hybridization, base stacking occurs which reduces the UV absorption of the nucleic acid. By monitoring UV absorption and the resulting increase in UV absorption that occurs during strand separation, one may assess the hybridization affinity of a nucleic acid for its complement.

The structure and stability of hybridization complexes may be further assessed using NMR techniques known to those skilled in the art.

A vast array of oligonucleotide analogs exist that achieve the same functionality as naturally occuring oligonucleotides. There is an extensive literature setting forth an almost limitless variety of modifications that can be used to generate oligonucleotide analogs. The phosphaphate, sugar, and/or base moieties may be modified and/or replaced by the introduction/removal of chemical groups and/or bonds. Many oligonucleotide analogs have superior properties to those of naturally occurring oligonucleotides. Such superior properties include, but are not limited to, increased hybridization affinity and/or resistance to degradation.

Phosphodiester Moiety Analogs

Numerous analogs to the naturally occurring phosphodiester backbone have been used in oligonucleotide design. Phosphorothioate, phosphorodithioate, and methylphosphonate are readily synthesized using known chemical methods. Because novel nucleotide linkages can be synthesized manually to form a dimer and the dimer later introduced into the oligonucleotide via automated synthesis, the range of potential backbone modifications is as broad as the scope of synthetic chemistry. For example, the oligonucleotide may be substituted or modified in its internucleotide phosphate residue with a thioether, carbamate, carbonate, acetamidate or carboxymethyl ester. While all of the backbone modifications that have been characterized are too broad to set forth, FIGS. 3A, 3B, 3C, and 3D illustrate some of the many backbone modifications that may be used in oligonucleotide analogs.

Unlike the naturally occuring phosphodiester moieties, many phosphodiester analogs have chiral centers. For example, phosphorothioates, methylphosphonates, phosphoramidates, and alkyl phosphotriesters all have chiral centers. One skilled in the art would recognize numerous other phosphodiester analogs that possess chiral centers. Because of the importance of stereochemistry in hybridization, the stereochemistry of phosphodiester analogs can influence the hybridization affinity of the oligonucleotide for its target.

Most phosophodiester backbone analogs exhibit increased resistance to nuclease degradation. In an embodiment, phosphorothioates, methyl phosphonates, phosphorimidates, and/or phosphotriesters are used to achieve enhanced nuclease resistance. Increased resistance to degradation may also be achieved by capping the 5' and/or 3' end of the oligonucleotide. In an embodiment, the 5' and/or 3' end capping of the oligonucleotide is via a 5'—5' and/or 3'—3' terminal inverted linkage.

Phosphorothioate oligodeoxynucleotides are relatively nuclease resistant, water soluble analogs of phosphodiester oligodeoxynucleotides. These molecules are racemic, but still hybridize well to their RNA targets. Stein, C., et al. (1991) Pharmac. Ther. 52:365–384.

Phosphorothioate oligonucleotides may be stereo regular, stereo non-regular or stereo random. A stereo regular phosphorothioate oligonucleotide is a phosphorothioate oligonucleotide in which all of the phosphodiester linkages or phosphorothiodiester linkages polarize light in the same direction. Each phosphorous in each linkage may be either an Sp or Rp diastereomer.

Sugar Moiety Analogs

Oligonucleotide analogs may be created by modifying and/or replacing a sugar moiety.

The sugar moiety of the oligonucleotide may be modified by the addition of one or more substituents. For example, one or more of the sugar moieties may contain one or more of the following substituents: amino-alkylamino, araalkyl, heteroalkyl, heterocycloalkyl, aminoalkylamino, O, H, an alkyl, polyalkylamino, substituted silyl, F, Cl, Br, CN, $CF_3$, $OCF_3$, OCN, O-alkyl, S-alkyl, SOMe, $SO_2Me$, $ONO_2$, NH-alkyl, $OCH_2CH=CH_2$, $OCH_2CCH$, OCCHO, allyl, O-allyl, $NO_2$, $N_3$, and $NH_2$.

Modification of the 2' position of the ribose sugar has been shown in many instances to increase the oligonucleotide's resistance to degradation.

For example, the 2' position of the sugar may be modified to contain one of the following groups: H, OH, OCN, O-alkyl, F, CN, $CF_3$, allyl, O-allyl, $OCF_3$, S-alkyl, SOMe, $SO_2Me$, $ONO_2$, $NO_2$, $N_3$, $NH_2$, NH-alkyl, or $OCH=CH_2$, OCCH, wherein the alkyl may be straight, branched, saturated, or unsaturated.

In addition, the oligonucleotide may have one or more of its sugars modified and/or replaced so as to be a ribose or hexose (i.e. glucose, galactose)

Further, the oligonucleotide may have one or more $\alpha$-anomeric sugars. The oligonucleotide may also have one or more L sugars.

Figure 4:
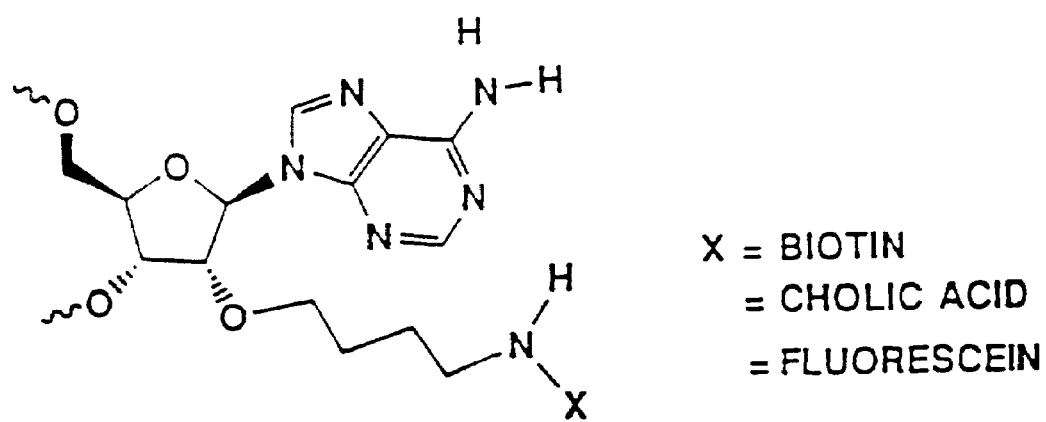
Figure 7:
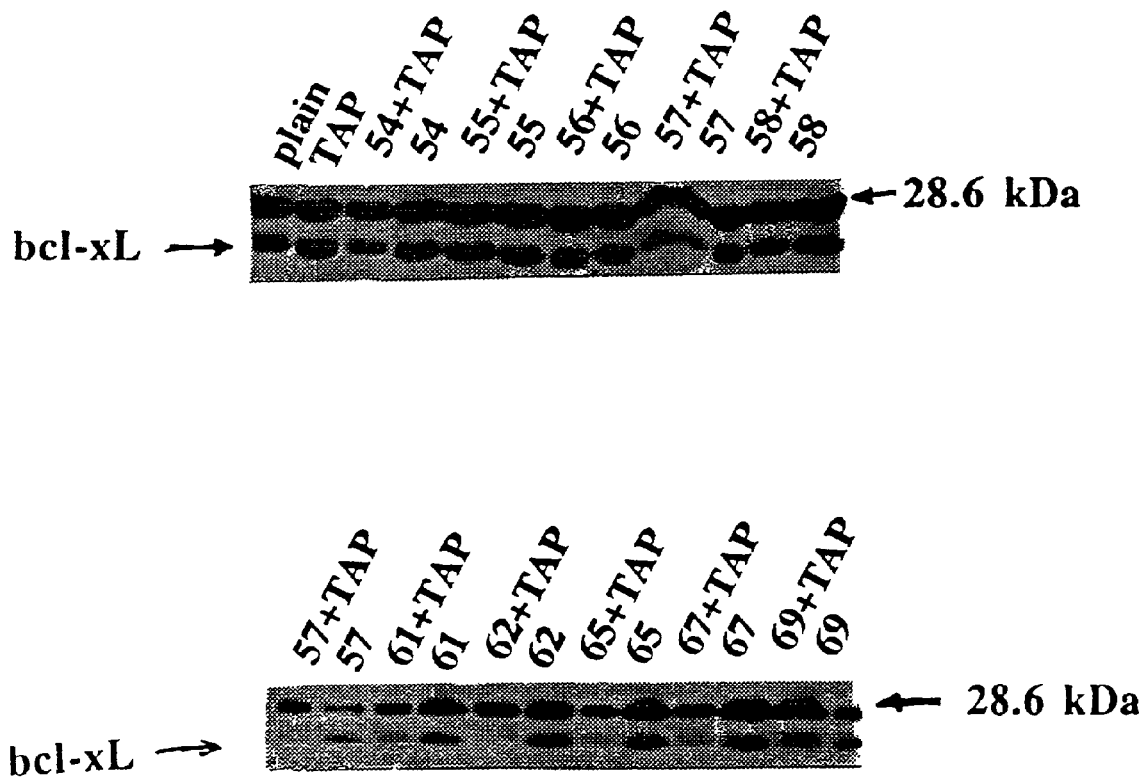
Figure 8:
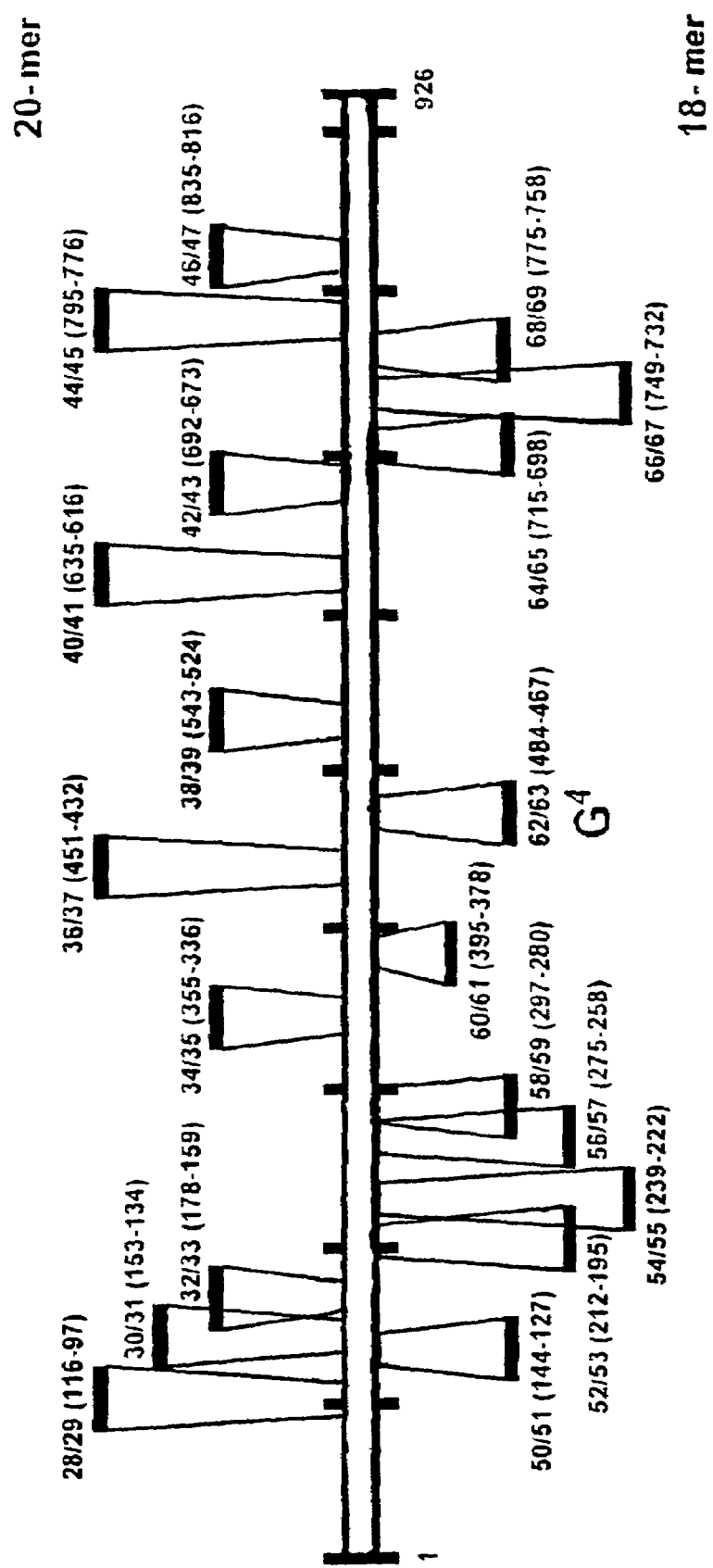
Figure 9:
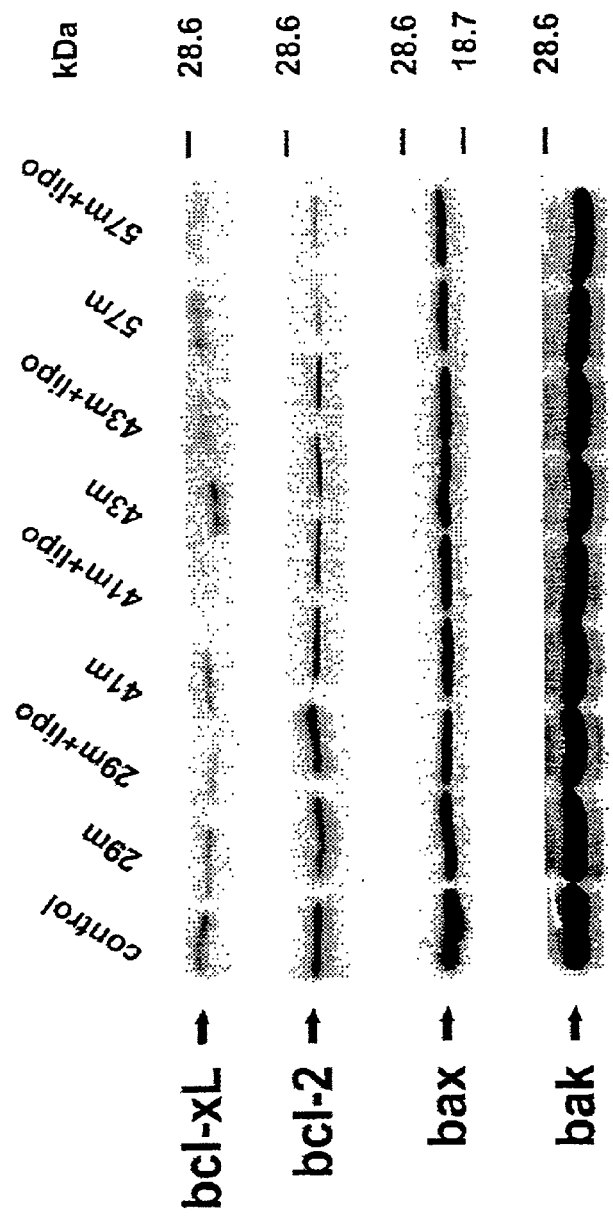
Figure 11:
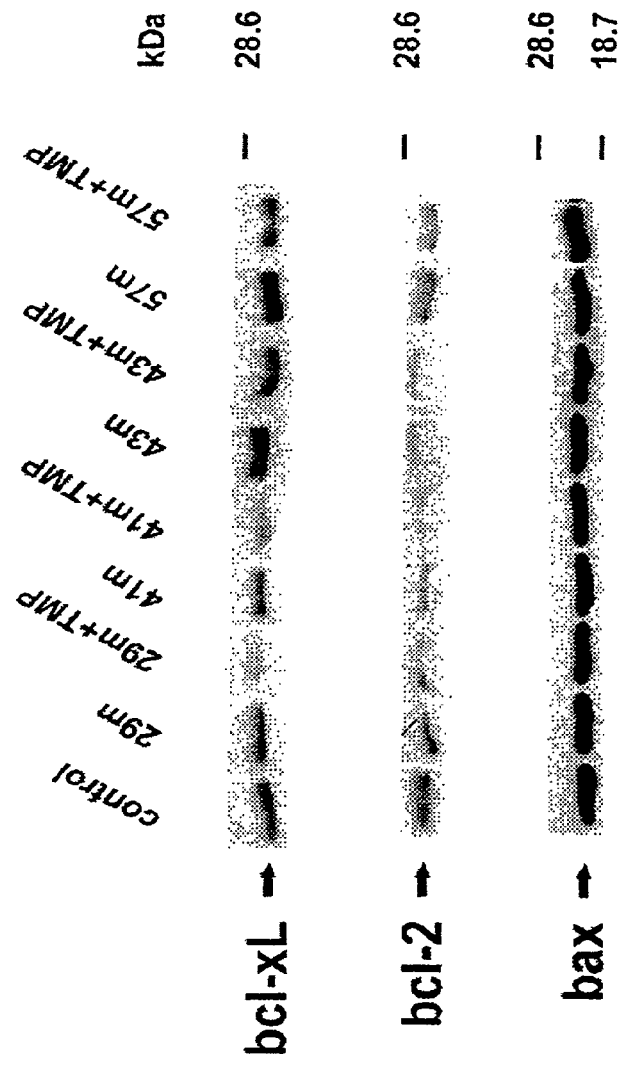
Figure 12:
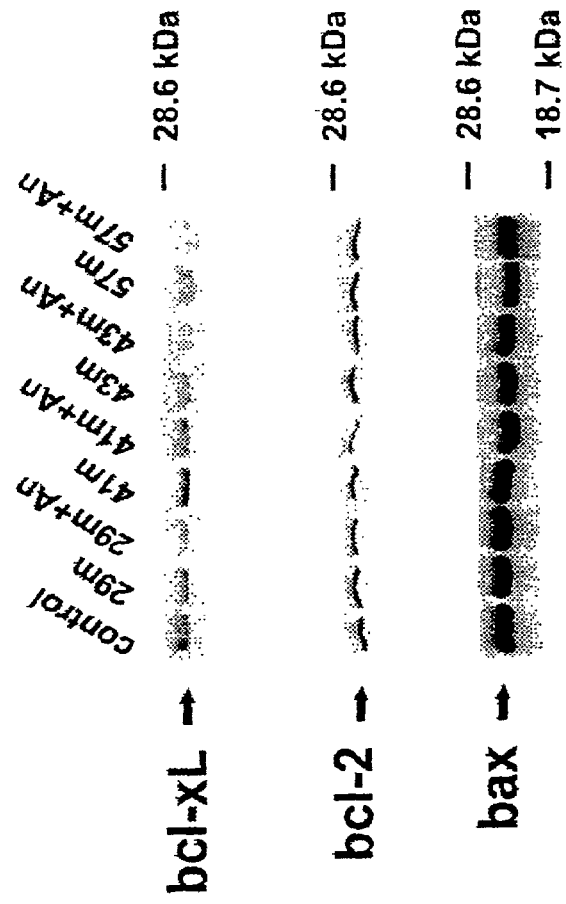
Figure 13:
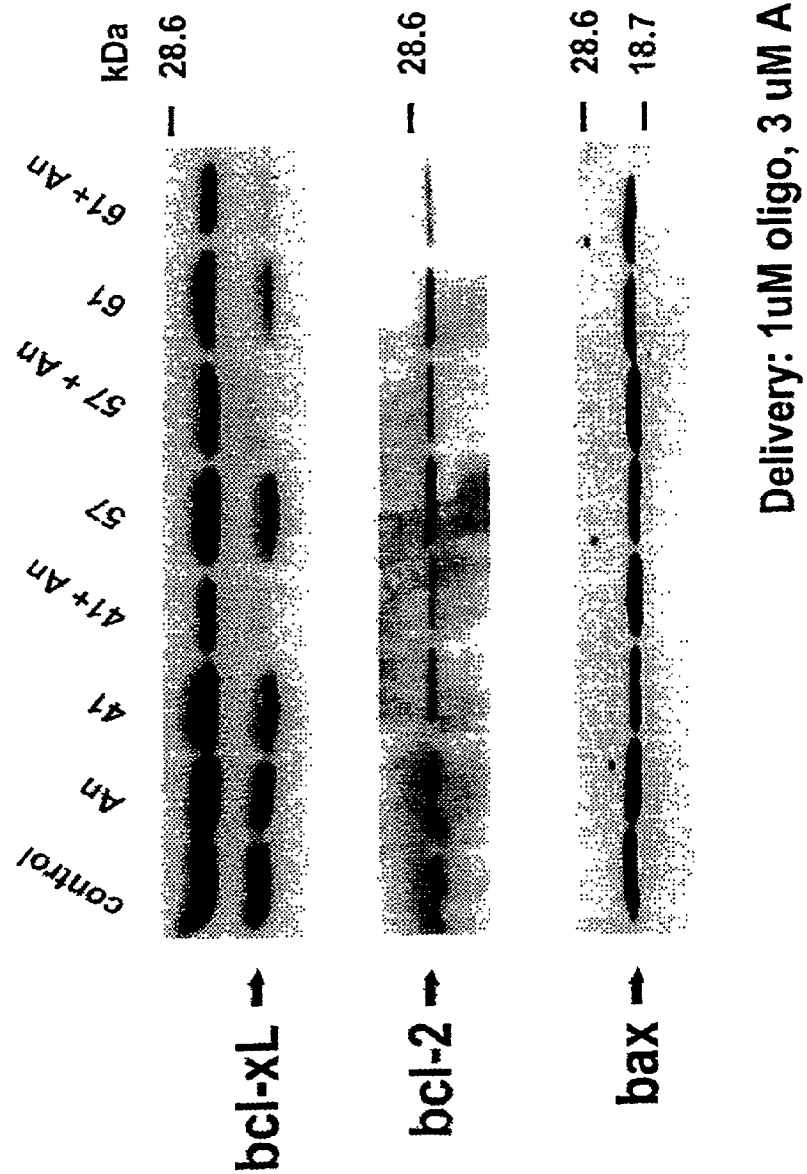
Figure 14:
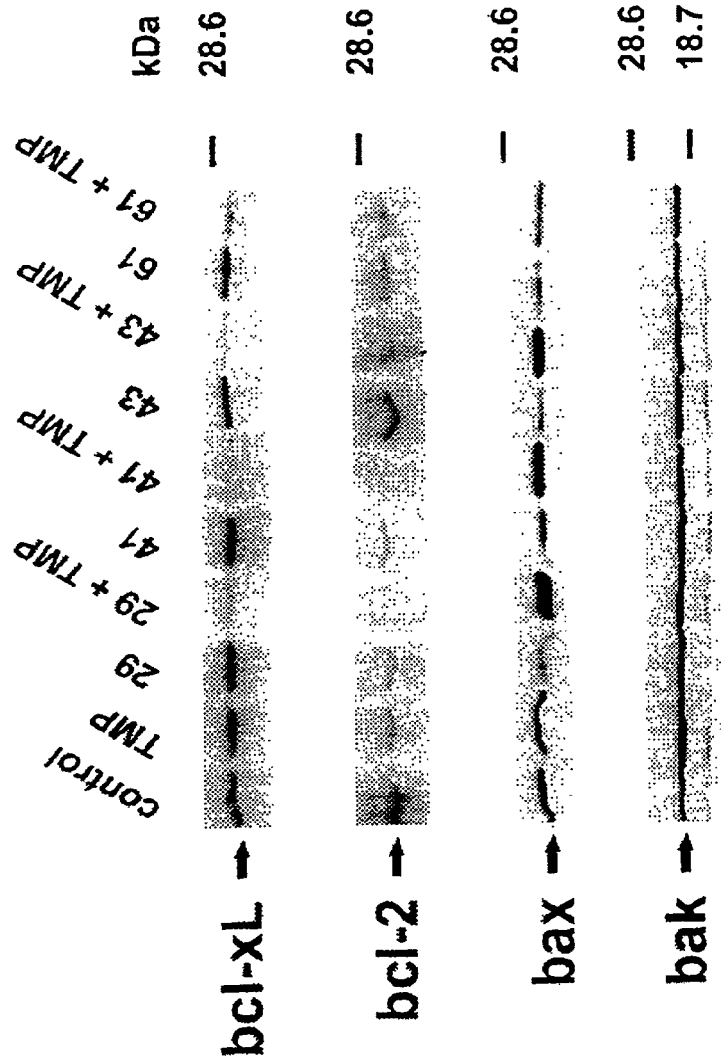
Figure 15:
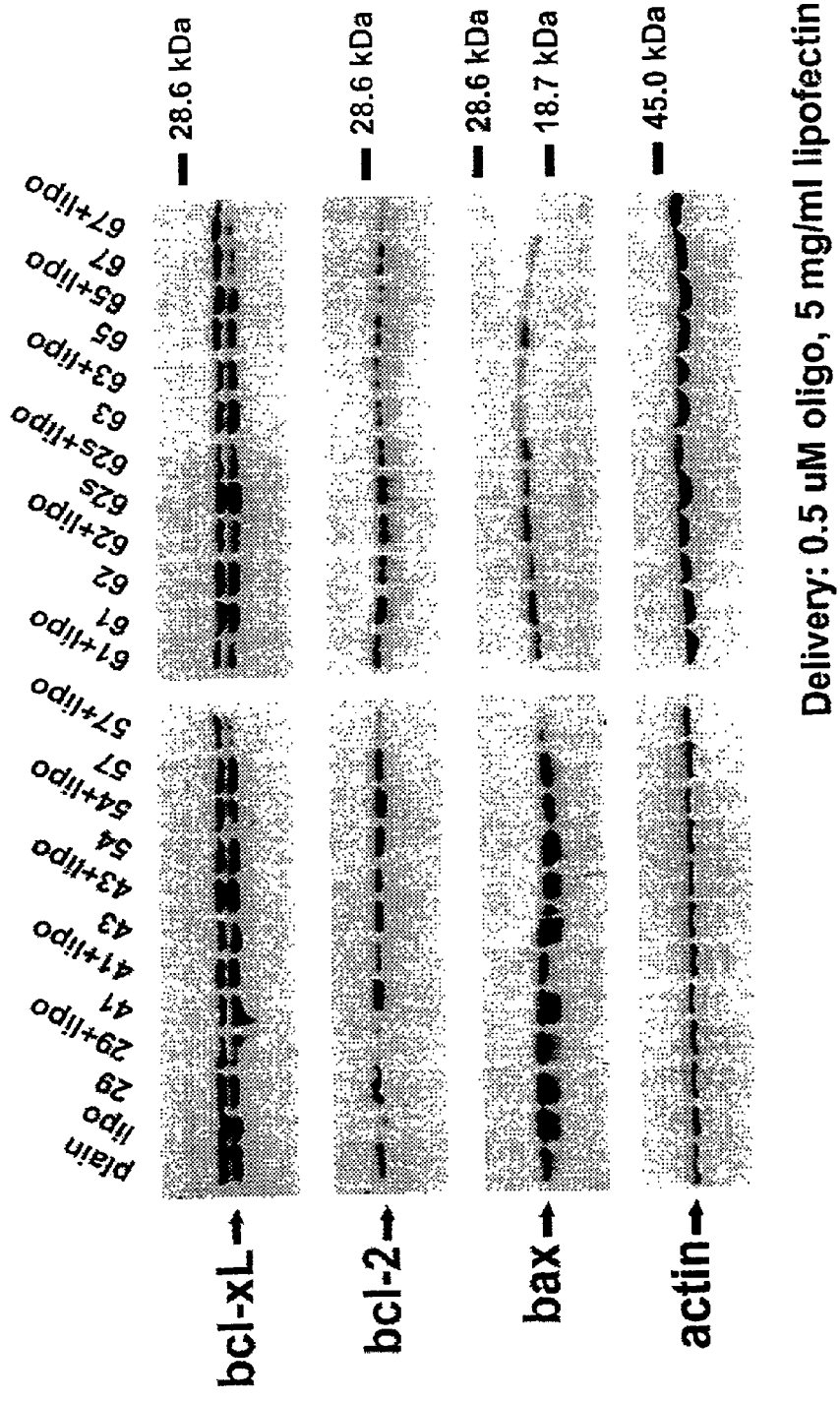
Figure 16:
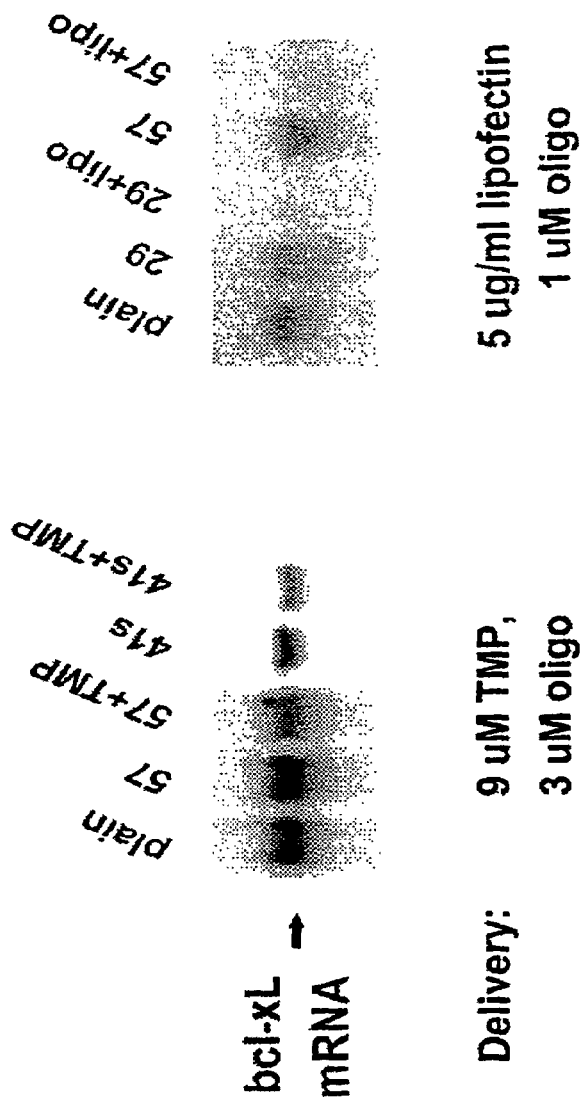

The sugar may be modified to contain one or more linkers for attachment to other chemicals such as fluorescent labels. In an embodiment, the sugar is linked to one or more aminoalkyloxy linkers. An example of a sugar containing an aminoalkyloxy linker is shown in FIG. 4. In another embodiment, the sugar contains one or more alkylamino linkers. Aminoalkyloxy and alkylamino linkers may be attached to biotin, cholic acid, fluorescein, or other chemical moieties through their amino group.

Base Moiety Analogs

In addition, the oligonucleotide may have one or more of its nucleotide bases substituted or modified. In addition to adenine, guanine, cytosine, thymine, and uracil, other bases such as inosine, deoxyinosine, hypoxanthine may be used. In addition, isoteric purine 2'deoxy-furanoside analogs, 2'-deoxynebularine or 2'deoxyxanthosine, or other purine or pyrimidine analogs may also be used. By carefully selecting the bases and base analogs, one may fine tune the hybridization properties of the oligonucleotide. For example, inosine nay be used to reduce hybridization specificity, while diaminopurines may be used to increase hybridization specificity.

Adenine and guanine may be modified at positions N3, N7, N9, C2, C4, C5, C6, or C8 and still maintain their hydrogen bonding abilities. Cytosine, thymine and uracil may be modified at positions N1, C2, C4, C5, or C6 and still maintain their hydrogen bonding abilities.

Some base analogs have different hydrogen bonding attributes than the naturally occurring bases. For example, 2-amino-2'-dA forms three (3), instead of the usual two (2), hydrogen bonds to thymine (T).

Examples of base analogs that have been shown to increase duplex stability include, but are not limited to, 5-fluoro-2'-dU, 5-bromo-2'-dU, 5-methyl-2'-dc, 5-propynyl-2'-dC, 5-propynyl-2'-dU, 2-amino-2'-dA, 7-deazaguanosine, 7-deazadenosine, and N2-Imidazoylpropyl-2'-dG. For purposes of illustration, several base analogs are shown in FIGS. 5A and 5B.

Pendant Groups

A "pendant group" may be linked to the oligonucleotide. Pendant groups serve a variety of purposes which include, but are not limited to, increasing cellular uptake of the oligonucleotide, enhancing degradation of the target nucleic acid, and increasing hybridization affinity. Pendant groups can be linked to any portion of the oligonucleotide but are commonly linked to the end(s) of the oligonucleotide chain. Examples of pendant groups include, but are not limited to: acridine derivatives (i.e. 2-methoxy-6-chloro-9-aminoacridine); cross-linkers such as psoralen derivatives, azidophenacyl, proflavin, and azidoproflavin; artificial endonucleases; metal complexes such as EDTA-Fe(II), o-phenanthroline-Cu(I), and porphyrin-Fe(II); alkylating moieties; nucleases such as amino-1-hexanolstaphylococcal nuclease and alkaline phosphatase; terminal transferases; abzymes; cholesteryl moieties; lipophilic carriers; peptide conjugates; long chain alcohols; phosphate esters; amino; mercapto groups; radioactive markers; nonradioactive markers such as dyes; and polylysine or other polyamines.

In one example, the oligonucleotide comprises an oligonucleotide conjugated to a carbohydrate, sulfated carbohydrate, or gylcan. Conjugates may be regarded as a way as to introduce a specificity into otherwise unspecific DNA binding molecules by covalently linking them to a selectively hybridizing oligonucleotide.

Cellular Uptake

To enhance cellular uptake, the oligonucleotide may be administered in combination with a carrier or lipid. For example, the oligonucleotide may be administered in combination with a cationic lipid. Examples of cationic lipids include, but are not limited to, lipofectin, dotma, dope, and Dogs. The oligonucleotide may also be administered in combination with a cationic amine such as poly (L-lysine). Oligonucleotide uptake may also be increased by conjugating the oligonucleotide to chemical moieties such as transferrin and cholesteryls. In addition, oligonucleotides may be targeted to certain organelles by linking specific chemical groups to the oligonucleotide. For example, linking the oligonucleotide to a suitable array of mannose residues will target the oligonucleotide to the liver.

The cellular uptake and localization of oligonucleotides may be monitored by using labeled oligonucleotides. Methods of labeling include, but are not limited to, radioactive and fluorescent labeling. Fluorescently labeled oligonucleotides may be monitored using fluorescence microscopy and flow cytometry.

The efficient cellular uptake of oligonucleotides is well established. For example, when a 20 base sequence phosphorothioate (PS) oligonulceotide was Injected into the abdomens of mice, either intraperitoneally (IP) or intravenously (IV). The highest concentrations of oligonucleotide accumulated in the kidney and liver, with only very small amounts being found in the brain. Chain-extended oligonucleotides were also observed. Argrawal, S., et al.(1988) Proc. Natl. Acad. Sci. U.S.A. 85:7079–7083. When the PS 27-oligonucleotide $\alpha$rev was given IV or to rats, the initial $T_{1/2\alpha}$ (transit out of the plasma) was 23 min, while the $T_{1/2\beta}$ of total body clearance was 33.9 hours. The long $\beta$ half-life of elimination demonstrates that dosing could be infrequent and still maintain effective, therapeutic tissue concentrations. Iverson, P. (1991) Anti-Cancer Drug Des. 6:531.

The efficacy of oligonucleotide therapy is also well established. For example, when a 24-base sequence PS oligonucleotide targeted to human c-myb mRNA was infused, through a miniosmotic pump, into scid mice bearing the human K562 chronic myeloid leukemia cell line, mean survival times of the mice treated with the antisense oligonucleotides were six- to eightfold longer than those of mice untreated or treated with the sense controls or treated with an oligonucleotide complementary to the c-kit proto-oncogene mRNA. Furthermore, significantly less tumor burden in the brain and ovary was observed histologically compared with the controls. After injecting IP 3'-PS-modified chimeric oligonucleotides that were complementary to the initiation codon region of the NF-κB mRNA (p65), a complete tumor involution was observed in 13 out of 13 antisense-treated mice. Untreated or sense-treated mice died by 12 weeks, where as the treated animals had no recurrence for at least 5 months. Ratajczak, et al. (1992) Proc. Natl. Acad. Sci. U.S.A. 89:11823.

This invention provides an antisense oligonucleotide or analog thereof comprising 10 or more contiguous bases or base analogs from the sequence of bases of sequence A, B, C, D, E, F, G, H, I, J, K, L, or M of FIG. 1.

This invention also provides an antisense oligonucleotide or analog thereof comprising a sequence having 90% of greater identity to sequence A, B, C, D, E, F, G, H, I, J, K, L, or M of FIG. 1.

This invention also provides an antisense oligonucleotide or analog thereof comprising a sequence having 85% of greater identity to sequence A, B, C, D, E, F, G, H, I, J, K, L, or M of FIG. 1.

This invention also provides an antisense oligonucleotide or analog thereof comprising a sequence having 80% of greater identity to sequence A, B, C, D, E, F, G, H, I, J, K, L, or M of FIG. 1.

This invention also provides an antisense oligonucleotide or analog thereof comprising a sequence having 75% of greater identity to sequence A, B, C, D, E, F, G, H, I, J, K, L, or M of FIG. 1.

This invention also provides an antisense oligonucleotide or analog thereof comprising a sequence having 70% of greater identity to sequence A, B, C, D, E, F, G, H, I, J, K, L, or M of FIG. 1.

This invention further provides an antisense oligonucleotide or analog thereof comprising nucleotide sequence A, B, C, D, E, F, G, H, I, J, K, L, or M of FIG. 1.

This invention also provides the above-described antisense oligonucleotides, wherein the nucleotide sequence comprises nucleotide sequence A, A', B, C, C', D, E, E', F, G, G', H, H', I, I', J, K, K', L, L', M, or M' of FIGS. 2A and 2B.

This invention further provides the above-described antisense oligonucleotides, wherein the oligonucleotide is conjugated to a peptide.

This invention also provides the above-described antisense oligonucleotides, wherein the oliaonucleotide is encapsulated in a liposome or nanoparticle.

This invention also provides the above-described antisense oligonucleotides, wherein the phosphate backbone comprises phosphorothioate bonds.

In addition, this invention provides the above-described antisense oligonucleotides, wherein the backbone is bonded to one or more lipid substituents.

This invention also provides the above-described antisense oligonucleotides, wherein one or more of the oligonucleotides's sugars contain an —OMe group at their 2' positions.

This invention further provides the above-described antisense oligonucleotides, wherein the phosphate backbone consists essentially of phosphorothioate bonds.

This invention also provides the above-described antisense oligonucleotides, wherein the phosphorothioate is stereo regular.

This invention also provides the above-described antisense oligonucleotides, wherein the oligonucleotide is linked to an intercalating agent, a cross-linker, an endonuclease, a lipophilic carrier, an alkylating agent, a coordination complex, or a peptide conjugate, or a combination thereof In addition, this invention provides the above-described antisense oligonucleotides, wherein the oligonucleotide is modified to reduce its ionic charge or increase its hydrophobicity.

In an embodiment, an alkyl group is attached to increase the hydrophobicity of the oligonucleotide. In another embodiment, one or more oxygen atoms are replaced by sulphur atoms to decrease the hydrophobicity of the oligonucleotide.

This invention also provides the above-described antisense oligonucleotides, wherein the oligonucleotide comprises one or more short chain alkyl structures that replace some of the oligonucleotide's phosphodiester bonds.

This invention further provides the above-described antisense oligonucleotides, wherein the oligonucleotide is linked to one or more cholesteryl moieties.

This invention also provides the above-described antisense oligonucleotides, wherein the oligonucleotides comprises one or more bases with a C-5 propynyl pyrimidine modification.

The above-described antisense oligonucleotide wherein the oligonucleotide comprises one or more bases with a C-5 propynyl pyrimidine modification.

This invention provides a method of treating cancer, comprising introducing into a tumor cell an effective amount of the antisense oligonucleotide of the above-described antisense oligonucleotide wherein the oligonucleotide comprises one or more bases with a C-5 propynyl pyrimidine modification, thereby reducing the levels of bcl-2 protein produced and treating cancer.

In an embodiment, the cancer is epithelial cancer. In a further embodiment, the epithelial cancer is prostate cancer. In still a further embodiment, the epithelial cancer is lung cancer, in still a further embodiment, the epithelial cancer is bladder cancer.

In a separate embodiment of the above method, the introducing comprises using a lipid as a delivery agent. In a further embodiment, the introducing comprises using porphyrin or lipofectin as a delivery agent.

In another embodiment, the effective amount is between 0.1 µM and 10 µM. In a further embodiment, the effective amount is between 0.1 µM and 4 µM. In a further embodiment, the effective amount is between 0.4 µM and 1 µM.

In addition, this invention provides a method of treating cancer, comprising introducing into a tumor cell an effective amount of the the above-described antisense oligonucleotide, thereby reducing the levels of bcl-xL protein produced and treating cancer. In an embodiment, the cancer being treated is epithelial cancer.

The actual effective amount will be based upon the size of the oligonucleotide, the biodegradability of the oligonucleotide, the bioactivity of the oligonucleotide and the bioavailability of the oligonucleotide. If the oligonucleotide does not degrade quickly, is bioavailable and highly active, a smaller amount will be required to be effective. The effective amount will be known to one of skill in the art; it will also be dependent upon the form of the oligonucleotide, the length of the oligonucleotide and the bioactivity of the polypeptide. One of skill in the art could routinely perform empirical activity tests to determine the bioactivity in bioassays and thus determine the effective amount.

This invention also provides the above-described methods, wherein the effective amount is between 0.1 µM and 10 µM. In an embodiment of the above-described method, the effective amount is between 0.1 µM and 4 µM.

In addition, this invention provides the above-described methods, wherein the effective amount is between 0.4 µM and 1 µM.

This invention further provides the above-described methods, wherein the cancer is epithelial cancer.

This invention also provides the above-described methods, wherein the epithelial cancer is prostate cancer.

This invention also provides the above-described methods, wherein the epithelial cancer is lung cancer.

In addition, this invention provides the above-described methods, wherein the epithelial cancer is bladder cancer.

This invention also provides the above-described methods, wherein the introducing comprises using a lipid as a delivery agent.

This invention further provides the above-described methods, wherein the introducing comprises using porphyrin or lipofectin as a delivery agent.

This invention also provides the above-described methods, wherein the effective amount is between 0.1 µM and 10 µM. In an embodiment of the above-described method, the effective amoutn is betwee 0.1 µM and 4 µM.

In addition, this invention provides the above-described methods, wherein the effective amount is between 0.4 µM and 1 µM.

This invention also provides a method of promoting the regression of vascular lesions, comprising introducing into a vascular cell an amount of the the above-described antisense oligonucleotides effective to reduce the levels of bcl-xL protein produced, thereby promoting the regression of vascular lesions.

This invention further provides the above-described methods, wherein the introducing comprises using a lipid as a delivery agent.

This invention also provides the above-described methods, wherein the introducing comprises using porphyrin or lipofectin as a delivery agent.

This invention also provides the above-described methods, wherein the effective amount is between 0.1 µM and 10 µM. In an embodiment of the above-described method, the effective amount is between 0.1 and 4 µM.

In addition, this invention provides the above-described methods, wherein the effective amount is between 0.4 µM and 1 µM This invention also provides a pharmaceutical composition comprising an effective amount of any of the above-described antisense oligonucleotides or analogs thereof and a pharmaceutically acceptable carrier.

Pharmaceutically acceptable carriers are well known to those skilled in the art and include, but are not limited to phosphate buffer and saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. preservatives and other additives may also be present, such as, for example, antimicrobials, antioxidants, chelating agents, inert gases and the like.

This invention further provides the above-described pharmaceutical compositions, wherein the effective amount is between 0.1 µM and 4 µM. In an embodiment of the above-described composition, the effective amount is between 0.1 µM and 4 µM.

In addition, this invention provides the above-described pharmaceutical compositions, wherein the effective amount is between 0.4 µM and 1 µM.

This invention also provides the above-described pharmaceutical compositions, wherein the oligonucleotide is encapsulated in a liposome or nanoparticle.

This invention further provides the above-described pharmaceutical compositions, wherein the pharmaceutical composition comprises tetra meso-(4-methylpyridyl)porphine or tetra meso-(anilinium)porphine or a combination thereof.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

First Series of Experiments

Forty 18- and 20-mer mixed phosphate/phosphorothioate backbone oligonucleotides with or without C-5-propyne pyrimidine modifications chosen by "walking" along the bcl-xL mRNA have been evaluated as to their ability to decrease bcl-xL protein expression in human prostate cancer cell lines (LNCaP, DU145 and PC3). The cell lines were obtained from the ATTC (Rockville, Md.). The cells were grown in RPMI 1640 media supplemented with 10% FBS in 5% CO2 atmosphere and routinely passaged when 90–95% confluent. All oligonucleotides were at least 95% full-length material when analysed by a reverse-phase HPLC.

Two novel agents for the intracellular delivery of oligonucleotides were used: tetra meso-(4-methylpyridyl)porphine (TMP) and tetra meso-(trimethylammonium)porphine (TAP). TMP and TAP both are cations which form 2:1 and 3:1 complexes with oligonucleotides. Human prostate carcinoma cells were plated in 6-well tissue culture dishes and next day (when 80–90% confluent) were washed once with OPTI-MEM and treated with prepared complex of oligonucleotide (1 µM) plus TMP (2 µM) or TAP (3 µM) for 4 h at 37° C. The cells were then washed once with RPMI-10% FBS and were allowed to recover in RPMI-10% FBS for another 20 h. At this time cells were washed twice with PBS and then protein and/or mRNA were extracted and analysed.

Western blot analysis demonstrated the effective downregulation of bcl-xL protein with five of the most active oligonucleotides (T31057, T31061, T31062, T31065, T31067). For the western blot analyses approximately $10^6$ cells were lysed for 30 min on ice in 100 µl of RIPA buffer (50 mM Tris-HCl, pH 8.0–150 mM NaCl —0.1% SDS—1% NP40—0.5% sodium deoxycholate). Aliguots of cell extracts containing 20 µg of protein were electrophoresed in 12% SDS-polyacrylamide gel and transferred to PVDF membrane (Millipore Corp., Bedford, Mass.). Filters were blocked and stained with an 1:200 dilution of rabbit anti-bcl-x polyclonal antibody (Santa Cruz Biotechnology Inc., Santa-Cruz, Calif.). After washing, filters were incubated in a 1:10,000 dilution of peroxidase-conjugated anti-rabbit secondary antibody (Amersham Life Sciences, Arlington Heights, Ill.). ECL was performed using the procedure recommended by the manufacturer and the filters were exposed to X-ray film.

Control oligonucleotides did not affect expression of bcl-xL and cell viability. The most active oligonucleotides are complementary to regions on the 3'-end of the bcl-xL mRNA. Moreover, C-5 propyne pyrimidine modified oligonucleotides seem to be more effective than pyrimidine unmodified.

These five active oligonucleotides (T31057, T31061, T31062, T31065, T31067) alone did not induce apoptosis in DU145 prostate cancer cell lines, as is shown with DAPI-staining. To determine the amount of apoptotic nuclei, cells were plated in 4-chamber tissue culture slides (Nunc, Inc., Naperville, Ill.) and after the experiment, were washed with PBS, fixed with 90% ethanol/ 5% acetic acid, and after 2 rinses with PBS, stained with a 1.5 mg/ml solution of DAPI in PBS. The slides were washed twice with PBS, mounted and photographed using a Nikon phase-fluorescence microscope.

In an attempt to approximate clinical drug resistance in prostate cancer a commonly used prostate cancer cell line, LNCaP, was genetically manipulated so that these cells would overexpress the human bcl-xL protein. This cell line is a popular model for the study of prostate cancer, because it retains some of the most prominent differentiated features of the human prostate cell. LNCaP cells also have proven to be growth responsive to androgen steroids in vitro. This bcl-xL overexpressing cell line provides a useful in vitro model for the subsequent study of drug resistant adenocarcinoma of the prostate gland.

The human prostate cancer cell line LNCaP was received from ATTC (Rockville, Md.). LNCaP cells were propagated as monolayer culture in RPMI 1640 supplemented with 10% FBS, in 5% CO2 atmosphere. Confluent cultures were routinely passaged approximately weekly, with RPMI 1640, containing 5 mM EDTA.

LNCaP cells transfected with the neomycin-selectable pSFFV/bcl-xL plasmid or with a control, neomycin-resistant expression vector pSFFV. Aliquots containing 10 µg of plasmid and 5 µg of lipofectin reagent (Life technologies, Inc., Gaithersburg, Md.) in serum-free OPTI-MEM (Life Technologies, Inc.) were added to cultured cells. The transfection media was replaced 4 h later with RPMI-10% FBS medium. Individual colonies were selected from these plates after approximately 3–4 weeks of routine maintenance in RPMI-10% FBS containing 0.6 mg/ml G418 sulfate (Geneticin, Life Technologies, Inc.). The bcl-xL-transformed LNCaP cells were cultured in RPMI-10% FBS, supplemented with 0.3 mg/ml G418 sulfate in 5% CO2 atmosphere.

Two clones of LNCaP cells overexpressing bcl-xL protein (1072-4 and 1072-5) have been obtained after transfection of wild type LNCaP cells with the plasmid vector pSFFV/bcl-xL and lipofectin. Also a mock transfectant clone of LNCaP cells carrying neo® resistance gene (1072-3) was used for the control experiments. Clone 1072-4 demonstrates 10-fold overexpression, and clone 1072-5—4-fold overexpression of bcl-xL protein. Western blot analysis for bcl-xL protein was performed as described above. Results for bcl-xL protein expression were confirmed by Northern blot analysis for bcl-xL mRNA expression, demonstrating significant elevation of this mRNA in bcl-xL transformed cell lines. For the Northern blot analysis, the total RNA was isolated from the cells using TRIZOL reagent (GIBCO BRL), and 20 µg aliquotes were separated in RNA-formaldehyde gel, blotted onto nylon membranes (Schleicher & Schull), UV-linked and prehybridized for two hours at 42° C. in the standard hybridization solution. Then the blot was hybridized overnight with the PCR-amplified fragment of human bcl-xL cDNA at 42° C. Dcl-xL coding fragment was amplified from pSFFV/bcl-xL plasmid using bcl-x specific primers. The primer sequences were: bcl-x-upstream, 5'-ATGTCTCAGAGCAACCGGGA-3' (SEQ ID NO:36); and bcl-x-downstream, 5'-TCATTTCCGACTGAAGAGTG-3' (SEQ ID NO:37). Twenty five cycles of amplification were performed in DNA Thermal Cycler (Perkin-Elmer, Norwalk, Conn.) at 94° C. (30 sec), 55° C. (30 sec), and 72° C. (30 sec). The PCR products were analysed on a 1.2% agarose gel. The resultant fragment was labeled by random primer method to the specific activity $10^7$ cpm/ng of the probe and used for the hybridization. After washings blots were autoradiographed for 24h at −80° C. Blots were stripped of radioactivity and reprobed with a $^{32}$P-labeled G3PDH probe to confirm the equal loading.

Overexpression of bcl-xL protein does not affect the relative growth rate of LNCaP cells in culture medium containing 10% FBS as determined by MTT assay. For this assay LNCaP cells were seeded in 24-well tissue culture plates. Next day after the experiment the old media was removed, the cells were washed once with PBS, and RPMI containing 0.5 mg/ml MTT (Sigma Co, St. Louis, Mo.) was added. The cells were incubated at 37° C. for 4 h, then solubilization solution (0.04N HCl in isopropyl alcohol) was added and optical density was measured at 540 nm.

Clonal derivatives of bcl-xL transfected LNCaP cells that were overexpressing high amounts of bcl-xL protein were resistant to taxol (up to 100 nM) and mitoxantrone (up to 4 µM) treatment for 24 h. These drugs have been shown to induce apoptosis in parental LNCaP cells or neomycin-expressing control-transfected LNCaP cells. This finding strongly supports the hypothesis that bcl-xL gene product is a factor in the development of chemotherapy resistance in hormone-refractory prostate cancer.

Antisense oligonucleotides provide an efficient means for bcl-xL protein elimination in prostate cancer cell lines. When antisense oligonucleotides were applied to the bcl-xL overexpressor, the down-regulation of this anti-apoptotic protein was not apparant. A possible way to down-regulate bcl-xL protein in such case could be using antisense oligonucleocide therapy in combination with chemotherapeutic drugs.

It has been shown recently (Am J Pathol 1996, 148: 1567–1576) that expression of several anti-apoptotic members of the bcl-2 family, including bcl-2 and bcl-xL proteins increases during progression of prostate cancers. our transfected clones overexpressing bcl-xL can mimic the clinical model of adenocarcinoma of the prostate gland. Demonstration of the mechanism of action of different drugs and their combinations with antisense oligonucleotides in these transfected LNCaP cells could help form the basis for a better understanding of prostate cancer.

Forty modified oligonucleotides complementary to the bcl-xL mRNA have been evaluated as to their ability to decrease bcl-xL protein expression in human prostate cancer cell lines (LNCaP, DU145, and PC3).

Two novel agents for the intracellular delivery of oligonucleotides were used: tetra meso(4-methylpyridyl)porphine (TMP) and tetra meso(trimethylammonium)porphine (TAP).

Western blot analysis demonstrated effective down-regulation of bcl-xL protein with five of the most active oligonucleotides (T31057, T31061, T31062, T31065, T31067).

These active oligonucleotides alone did not induce apoptosis in DU145 cells.

Two clones of LNCaP cells overexpressing bcl-xL protein and clone carrying neo resistance gene only have been obtained after transfection of wild type LNCaP cells with the plasmid vectors pSFFV/bcl-xL and pSFFV.

Overexpression of bcl-xL protein and mRNA has been shown by western and northern blot analyses.

Overexpression of bcl-xL protein does not affect the relative growth rate of LNCaP cells in culture medium containing 10% FBS.

Bcl-xL overexpressing clones of LNCaP cell lines demonstrated high resistance to taxol (100 nM) and mitoxantrone (4 µM) treatment.

Active antisense oligonucleotides do not down-regulate bcl-xL protein in the LNCaP clones overexpressing bcl-xL.

Second Series of Experiments

Bcl-xL in Prostate and Bladder Cancer Cells: Cheosensitization after Downregulation by Treatment with Directed ("Antisense") Oligonucleotides Introduction This study demonstrated the role of bcl-xL and bcl-2 proteins for the regulation of the sensitivity of cancer cells to different drugs, including taxanes and antracyclines. In conclusion, it was demonstrated that treatment with bcl-xL antisense oligonucleotides induces sensitization of prostate and bladder carcinoma cell lines to chemotherapy treatment, suggesting that Bcl-xL provides one of the defending mechanisms for cancer cells allowing them to tolerate chemotherapeutic treatment.

Several pathways have been described that regulate programmed cell death (apoptosis). One these implicates bcl-2 family proteins as critical in apoptosis commitment. The bcl-2 family includes several homologous proteins that may be either pro- or antiapoptotic. Bcl-2 and bcl-xL are anti-apoptotic, whereas bax promotes apoptosis. Together, these proteins form a complex network of heterodimers and homodimers that govern the relative sensitivity of a cell to potentially apoptotic stimuli.

Bcl-x is a relatively new member of the bcl-2 family of apoptosis-related proteins, and its expression has been detected in a range of normal tissues, particularly in the central nervous system and thymus. Immunocytochemical studies have demonstrated that the bcl-x protein can be detected in numerous tumor cell lines as well. Expression has also been found in the epithelial cells of the normal prostate (Krajewski, et al., Cancer Res 1994; 54: 5501–5507), where, it is speculated, it contributes to the hormone-dependent control of programmed cell death. Krajewski, et al., (1996) found that 64/64 (100%) of cases of adenocarcinoma of the prostate stained positively for bcl-x protein. Staining intensity seemed to be correlated with increasing Gleason score and the presence of metastases. Bcl-xL protein expression has also been demonstrated in 50% of clinical specimens of low stage bladder tumors (Gazzaniga, Oncol. Rep. 1998 5,901–04)

Since bcl-xS appears not to be expressed either in prostatic tumors, or in prostate cell lines in tissue culture, this staining most likely originates from bcl-xL. This 25.6 kDa protein has been shown in a number of cell lines to be a potent protector of cellular apoptosis induced by antineoplastic agents (Kim, 1997). When transferred into the murine IL-3-dependent prolymphocytic line FL5.12, bcl-xL greatly reduced the pro-apoptotic effects of bleomycin, cisplatin, etoposide, vincristine and doxorubicin (Ibrado, 1997; Minn, et al., 1995). In U937 cells, inhibitory effects on camptothecin-induced apoptosis were shown to be dependent on the intracellular concentration of bcl-xL protein. Diminution of cell death in response to etoposide, vinblastine, paclitaxel and cisplatinum were also observed (Schmitt, Exp. Cell Res. 1998 240 107–21). Bcl-xL can also block cellular apoptosis in settings in which bcl-2 is ineffectual (Gottschalk, PNAS 1994 91 7350). Several agents, such as butyrate in human fibroblasts (Chung, Rad Res. 149, 187 (1998), and paclitaxel in LNCaP and PC3 human prostate cancer cells (Liu) induce apoptosis that can be correlated with substantial decreases in the expression of bcl-xL protein. In the latter case, this occurred in the absence of any decrease in bax, bak, fas or fas ligand expression.

Bcl-2 protein expression has been found in 66% of low stage bladder tumors and 100% of high stage tumors. Expression is also found quite extensively in primary prostate cancer specimens (McConnell, 1992), although it has been observed in only 33% of samples of prostate tumors obtained from the bone marrow of patients with hormone-refractory disease (McDonnell J. Urol. 1997 569–574). At the present time, it appears that bcl-xL and bcl-2 have similar antiapoptotic function, and it is not clear why both are expressed in at least some prostate cancer cells. Notwithstanding, based on these data it is possible that overexpression of bcl-xL and bcl-2 protein might be factors enabling prostate cancer cells to survive in an androgen-deprived environment.

Materials and Methods

Reagents

Taxol and etoposide are products of Bristol-Myers Squibb, Princeton, N.J. Taxotere is a product of Rhone-Poulenc Rorer, Collegeville, Pa. Polysorbitan-80 and EL-cremophor, the carriers to taxotere and taxol, respectively, were obtained from Sigma (Milwaukee, Wis.). Mitoxantrone was from Immunex (Seattle, Wash.), and vinblastine was from Eli Lilly (Indianapolis, Ind.)

Cell Culture and Transformation of Cell Lines with Bcl-xL Plasmid Human PC3 and LNCaP prostate cancer cell lines, and the T24 bladder carcinoma cell line were obtained from American Type Culture Collection (Rockville, Md.). They were grown in RPMI 1640 medium (Gibco BRL, Grand Island, N.Y.), containing 10% (v/v) heat inactivated (56° C.) fetal bovine serum (FBS) (Gibco BRL, Grand Island, N.Y.), supplemented by 1% non-essential amino acids, 1% pyruvate, and 100 units/mL penicillin G sodium and 100 mg/mL streptomycin sulfate. All cell lines were cultured in 5% $CO_2$ atmosphere and were routinely passaged when 90–95% confluent.

LNCaP cells were transfected with the neomycin-selectable pSFFV/bcl-xL plasmid (obtained from Dr. Stanley Korsmeyer, Washington University School of Medicine, St. Louis, Mo.) or with a control, neomycin-resistant expression vector PSFFV. Aliquots containing 10 µg of plasmid and 5 µg of Lipofectin, reagent (Life technologies, Inc., Gaithersburg, Md.) in serum-free OPTI-MEM (Life Technologies, Inc.) were added to a cultured cells. The transfection media was replaced 4 h later with RPMI-10% FBS medium. Individual colonies were selected from these plates after approximately 3–4 weeks of routine maintenance in RPMI-10% FBS containing 0.6 mg/ml G418 sulfate (Geneticin, Life Technologies, Inc.). The bcl-xL-transformed LNCaP cells were cultured in RPMI-10% FBS, supplemented with 0.3 mg/ml G418 sulfate in 5% $CO_2$ atmosphere.

Oligonucleotides

Mixed-phosphate backbone (phosphorothioate and phosphodiester) oligonucleotides with or without C-5 propynyl modified pyrimidines, complementary to different regions of bcl-xL mRNA were obtained from The Aronex Pharmaceuticals Inc. (Woodland, Tex.). All oligonucleotides were 95% full-length material when analysed by a reverse-phase HPLC.

Treatment of cells with oligonucleotide-Lipofectin, or oligonucleotide-porphyrin complexes Prostate and bladder carcinoma cells were seeded the day before experiment in 6-well plates at density $3 \times 10^5$ cells per well (to be 80–90% confluent on the day of the experiment).

Oligonucleotides were delivered to the cells in the form of complexes with cationic lipid Lipofectin, (GIBCO BRL, Gaithersburg, Md.) or cationic porphyrins. In the first case equal volumes of oligonucleotide (5 mM) and Lipofectin, (5 mg) in reduced serum OPTI-MEM medium (GIBCO BRL, Gaithersburg, Md.) were mixed and allowed to form a complex for 30 min at room temperature. The mixture was diluted 1:9 with OPTI-MEM media and added to T24 cells rinsed with OPTI-MEM medium. The final concentrations were 1 mM for oligonucleotide and 5 mg/ml for Lipofectin. Control cells were treated with equivalent concentration of Lipofectin, or medium alone. Cells were incubated at 37° C. for 5 hours, then medium was replaced for McCoy 5A supplemented with 10.% FBS.

For cationic porphyrin delivery, oligonucleotide was premixed with TAP or TMP in OPTI-MEM medium to the final concentrations described in the Results for each cell line. Complex was formed for 15 min at room temperature, cells were washed once with OPTI-MEM and treated with prepared complex for 4 h at 37° C. Then cells were washed once with RPMI-10% FBS and were allowed to recover in RPMI-10% FBS for another 20 h. At this time cells were washed twice with PBS and then protein and/or mRNA were extracted as described and analyzed.

Western Blot Analysis

Cells treated with oligonucleotide—porphyrine or oligonucleotide—Lipofectamin, complex were washed twice with cold PBS and lysed on ice for 30 min in 100 ml of cold RIPA buffer [50 mM Tris-HCl (pH 8.0), 150 mM NaCl, 0.1% SDS, 1% NP40, and 0.5% sodium deoxycholate] with freshly added 0.1 mg/ml phenylmethylsulfonyl fluoride, 1 mM sodium orthovanadate, and 1 mg/ml aprotinin. Cell debris were removed by centrifugation at 14,000g for 10 min at 4° C. Protein concentrations were determined using the Bio-Rad protein assay system (Bio-Rad Laboratories, Richmond, Calif.).

Aliquots of cell extracts containing 20–50 mg of total protein were resolved in 12% SDS-PAAG and transferred to Immobilon-P PVDF membranes (Millipore Corp., Bedford, Mass.). Filters were blocked for 1 h at room temperature in Blotto A [5% nonfat milk powder in TBS-T: 10 mm Tris-HCl (pH 8.0), 150 mM NaCl, 0.05% Tween 20], and then incubated for 1 h at room temperature in Blotto A containing a 1:200 dilution of either rabbit anti-Bcl-xL, anti-Bax, or anti-Bak polyclonal antibodies or mouse anti-Bcl-2 mAb (all from Santa Cruz Biotechnology Inc., Santa Cruz, Calif.). After washing in TBS-T buffer (3×5 min, room temperature), filters were incubated for 45 min at room temperature in Blotto A containing a 1:10,000 dilution of corresponding peroxidase conjugated anti-rabbit or anti-mouse secondary antibody (Amersham, Arlington Heights, Ill.). After washing in TBS-T, ECL was performed according the recommendation of the manufacturer.

RNA Isolation and Northern Blot Analysis.

Total RNA was isolated from 5×107 cells using RNeasy Mini kit from QIAGEN (Santa-Clarita, Calif.). Forty μg of total RNA were electrophoresed on a 1% denaturing agarose gel containing formaldehyde, transferred to a Nytran-Plus nylon membranes (Schleicher&Schuell, Keene, N.H.) and covalently bound to a membrane by UV-irradiation. A bcl-xl coding region cDNA fragment generated by PCR and 32P—labeled by random primer method was hybridized to the filter-bound RNA in 50% formamide, 5×SSC, 5× Denhardt solution, 0.5% SDS and 0.1 mg/ml sonicated salmon sperm DNA overnight at 42° C. The membrane was washed 3 times for 15 min in 1×SSC, 0.1% SDS at 42° C., and 3 times for 10 min in 0.1×SSC, 0.1% SDS at 65° C. The filter was exposed to Kodak X-ray film with intensifying screens for 3 days at −70° C. and developed.

MTT Assay for Determination of Cell Viability.

The cytotoxicity of the combinations of drugs with oligonucleotides was determined by measurement of cell viability by use of colorimetric MTT assay.

LNCaP cells were seeded in 48-well tissue culture plates and treated next day subsequently with oligonucleotides and drugs at indicated concentration as described in Results. Then drug-contained media was removed, and the cells were washed once with PBS. Corresponding culture media (RPMI for prostate and McCoy 5A for bladder cancer cells) containing 0.5 mg/ml MTT (Sigma Co, St. Louis, Mo.) was added to each well. The cells were incubated at 37° C. for 4 h, then equal amount of solubilization solution (0.04N HCl in iso-propyl alcohol) was added to each well and mixed thoroughly to dissolve the crystals of MTT formazan. After all crystals were dissolved, the plates were read on a Dynatech MR600 Microplate Reader, using a wavelength of 540 nm.

Results

PS-PO Oligonucleotides Directed Against Bcl-xL mRNA.

In the present study we have used an antisense strategy for the down-regulation of bcl-xL in prostate cancer cell lines. Forty oligonucleotides (twenty 20-mers and twenty 18-mers) have been chosen by the "walking along the mRNA" method. An arrangement of the oligonucleotides on Bcl-xL mRNA is shown on Scheme 1, where numbers reflected the base positions of the oligonucleotides. Each oligonucleotide has been assigned a number for further convenience and will be mention in the text according to this number. oligonucleotides have mixed phosphorothioate-phosphodiester backbone. Oligonucleotides with even numbers have regular heterocyclic bases whereas odd numbers oligonucleotides included C-propynyl modified cytosin and tymidine bases. Oligonucleotides were screened for their antisense activity to down-regulate Bcl-xL protein expression using Western blot analysis.

Optimal Conditions for the Delivery of Oligonucleotides within the Cells

To deliver oligonucleotides into cells we have used two different types of the delivery agents: lipids, such as Lipofectin, and cationic porphyrins (tetra meso-(4-methylpyridyl)porphine (TMP) and tetra meso-(trimethylammonium) porphine (TAP)).

Lipofectin, has been used to transfect T24 cells with antisense olgonucleotides. The optimal condition for the delivery was 5 mg/ml Lipofectin, and 0.5 μM of oligonucleotide in reduced serum OPTI-MEM medium. Unfortunately, with prostate cancer cell lines Lipofectin, did not demonstrate out good results because of high cytotoxicity. To deliver oligonucleotides into LNCaP and PC-3 cell line cationic porphyrins have been used. Porphyrins are novel class of agents for the intracellular delivery of oligonucleotides. They have been investigated by confocal microscopy and flow cytometry methods. It has been demonstrated that they form complexes with oligonucleotides and deliver them to the cell nucleus, where the porphyrin had completely dissociated from the oligonucleotide. No non-specific cytotoxic effects has been observed after the using of the porphyrins as delivery agents. Porphyrins demonstrated different activity in different cell lines. The optimal conditions for LNCaP cells were 3 µM of TAP and 1 µM of oligonucleotide; for PC-3 cells—7µM of TMP and 2 µM of oligonucleotide; and for T24 cells—9 µM of TMP and 3 µM of oligonucleotide. After cell treatment with the oligonucleotides, total protein was harvested and level of Bcl-xL protein expression was determined comparing to the untreated cells.

Evaluation of Bcl-xL Protein Levels by Western Blotting

The Bcl-xL protein was detected as a doublet with a molecular weight ranging from 29–31 kDa, a finding consistent with previous reports. During the screening of forty oligonucleotides, treatment with several sequences produced significant reductions in the steady-state levels of Bcl-xL protein expression. Compare to the untreated cells or cells treated with inactive oligonucleotides, the level of Bcl-xL expression decreases to 5–30% in case of the most active oligonucleotides. Some sequences provide moderate reduction of the Bcl-xL expression. A 19 kDa band which would correspond to the Bcl-xS protein was not detected in studied cells. Level of actin (control protein) remains unchanged al the times (Data are not shown). The oligonucleotide treatment also did not cause reductions in the total amount of protein, nor did it inhibit the growth of these cells, as was demonstrated by MTT assay.

Down-Regulation of Bcl-xL Protein and mRNA Expression with PS-PO Oligonucleotides in Different Cell Lines Screening of oligonucleotide set revealed several the most active oligonucleotides (numbers 29, 41, 43, 57, 61, 62 and 63). They decreased bcl-xL protein expression to 5–30% in tissue culture comparing to the untreated cells or cells, treated with oligonucleotides along, without delivery agent. To address the question of the mechanism of action of those oligonucleotides, we studied bcl-xL mRNA expression in treated and untreated cells by the Northern hybridization method, using bcl-xL cDNA fragment as a probe. A putative antisense mechanism of action for the majority of the active oligonucleotides (29, 41, 43, 57 and 61) is supported by the fact of down-regulation of Bcl-xL mRNA level. Oligonucleotides 62 and 63 possess a G-quartet and are likely not specific. In our further experiments we were not using those non-specific oligonucleotides. Considering the position of the active oligonucleotides on the bcl-xL mRNA, it can be assumed that those oligonucleotides are complementary to the most open (and so the most accessible for the RNase H action) mRNA regions.

C-propyne-modified oligonucleotides potentiate bcl-xL down-regulation. The ability of oligonucleotides to down-regulate bcl-xL protein expression differs in different cell lines (Data are not shown). The efficiency of the oligonucleotide is highly dependent on the delivery agent. Identical oligonucleotides demonstrated different bcl-xL down-regulation when delivered with different agents. However, it has to be emphasized that if oligonucleotide is active, it is active in any cell line, with any delivery agent.

Since the ability of cell to undergo apoptosis is determined by the ratio between anti- and proapoptotic members of bcl-2 family, we investigated if the treatment of the cells with antisense bcl-xL oligonucleotides affects the other related proteins. Our results demonstrated that there is not a unique action of bcl-xL antisense oligonucleotides on bax and bcl-2 proteins. The result is highly dependent on the cell line, the delivery agent and on the oligonucleotide sequence (Table 1). Cationic porphyrin-mediated delivery appears to provide increased specificity of oligonucleotide action. Oligonucleotides 29, 41 and 43, when delivered with TMP caused down-regulation of both anti-adoptotic proteins bcl-xL and bcl-2, but upregulated the proapoptotic protein bax in all studied cell lines (however, oligo 29 does not show significant activity in the T24 bladder cell carcinoma cell line with TMP delivery). It is suggested that treatment of the cells with oligonucleotides 29 and especially 41 and 43, can stimulate apoptotic processes within the cells and hence make cells more sensitive to chemotherapy treatment. MTT assay demonstrated that treatment of the cells with oligonucleotides alone caused decrease of cell viability. Preliminary experiments with oligo 43 demonstrated a two-fold sensitization of the PC3 and T24 cell lines to treatment by mitoxantrone compare to the control (treated with drug only) cells. This effect is highly visible at low drug concentration (less than 0.5 µM) and less obvious at high concentrations of mitoxantrone. Although oligonucleotide 57 makes cells more sensitive to chemotherapy, the effect is less pronounced. Oligonucleotide 45 does not cause bcl-xL down-regulation and does not sensitize cells to mitoxantrone treatment.

TABLE 1

Regulation of Bcl-Family Protiens Expression with Chimeric PS-PO Oligonucleotides in Prostate and Bladder Cancer Cell Lines

| | PC-3 Cell Line | | | LNCaP Cell Line | | | T24 Cell Line | | | | | |
|---|---|---|---|---|---|---|---|---|---|---|---|---|
| | TMP | | | TAP | | | lipofectin | | | TMP | | |
| | bcl-xL | bax | bcl-2 | bcf-xL | bax | bcl-2 | bcl-xL | bax | bcl-2 | bcl-xL | bax | bcl-2 |
| 29 | ↓ | ↑ | ↓ | ↓ | ↑ | ↓ | ↓ | ↓ | ↓ | — | — | — |
| 41 | ↓ | ↑ | ↓ | ↓ | — | ↓ | — | ↓ | ↓ | ↓ | ↑ | ↓ |
| 43 | ↓ | ↑ | ↓ | ↓ | ↑ | ↓ | — | ↓ | — | ↓ | ↑ | ↓ |
| 57 | ↓ | ↓ | ↓ | ↓ | ↓ | ↓ | ↓ | ↓ | ↓ | ↓ | ↓ | — |
| 61 | ↓ | ↓ | ↓ | ↓ | ↓ | ↓ | ND | ND | ND | ND | ND | ND |
| 62 | ↓ | ↑ | — | ↓ | ↑ | — | ↓ | ↑ | — | ↓ | ↑ | ↓ |
| 62s | ↓ | ↑ | — | ↓ | ↓ | ↓ | — | ↑ | ↓ | ↓ | ↑ | — |
| 63 | ↓ | — | — | ↓ | — | — | — | — | — | ↓ | ↑ | ↑ |

Marked reductions in Bcl-xL protein were detectable within 24 hours of additions of active oligonucleotides to LNCaP (60% reduction) and T24 cells (90% reduction), based on estimates using Western Blot analysis. Reductions of more than 80% in the relative levels of Bcl-2 protein in T24 cells treated with antisense oligonucleotides occurred also within 24 hours after treatment with antisense oligonucleotides. Thus, reductions in both proteins levels after antisense oligonucleotides treatment occur simultaneously. That allowed us to use an effect of oligonucleotide-mediated down-regulation of anti-apoptotic proteins Bcl-xL and Bcl-2 to sensitize cells to chemotherapy.

What is claimed is:

1. A composition of matter comprising an antisense oligonucleotide comprising 10 or more contiguous bases of the nucleotide sequence set forth in any one of SEQ ID NOS: 1 and 3–10 and 12–13 wherein the oligonucleotide is conjugated to a peptide and wherein the oligonucleotide is complementary to a human bcl-xL-encoding mRNA and inhibits translation thereof.

2. An antisense oligonucleotide consisting of the nucleotide sequence set forth in SEQ ID NO: 2 wherein the oligonucleotide is conjugated to a peptide and wherein the oligonucleotide is complementary to a human bcl-xL-encoding mRNA and inhibits translation thereof.

3. A composition comprising an effective amount of an antisense oligonucleotide of claim 1 and a pharmaceutically acceptable carrier, wherein the effective amount is between 0.1 µM and 10 µM.

* * * * *